(12) United States Patent
Hlavka et al.

(10) Patent No.: US 8,731,672 B2
(45) Date of Patent: *May 20, 2014

(54) SYSTEM AND METHOD FOR BRONCHIAL DILATION

(71) Applicant: Holaira, Inc., Plymouth, MN (US)

(72) Inventors: Edwin J. Hlavka, Minneapolis, MN (US); Lynn Elliott, Maple Grove, MN (US)

(73) Assignee: Holaira, Inc., Plymouth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/920,801

(22) Filed: Jun. 18, 2013

(65) Prior Publication Data

US 2013/0345700 A1 Dec. 26, 2013

Related U.S. Application Data

(63) Continuation of application No. 13/523,223, filed on Jun. 14, 2012, now Pat. No. 8,489,192, which is a continuation of application No. 12/372,607, filed on Feb. 17, 2009, now Pat. No. 8,483,831.

(60) Provisional application No. 61/049,605, filed on May 1, 2008, provisional application No. 61/066,026, filed on Feb. 15, 2008.

(51) Int. Cl.
*A61N 1/00* (2006.01)
*A61B 5/08* (2006.01)

(52) U.S. Cl.
USPC ............... 607/42; 607/2; 607/116; 607/118; 600/529

(58) Field of Classification Search
USPC .................. 607/2, 42, 116, 118; 600/529
See application file for complete search history.

(56) References Cited

U.S. PATENT DOCUMENTS

| | | |
|---|---|---|
| 612,724 A | 10/1898 | Hamilton |
| 1,155,169 A | 9/1915 | Starkweather |
| 1,207,479 A | 12/1916 | Bisgaard |
| 1,216,183 A | 2/1917 | Swingle |
| 1,695,107 A | 12/1928 | Kahl |
| 2,072,346 A | 3/1937 | Smith |
| 2,279,714 A | 4/1942 | Meyerhof et al. |
| 3,320,957 A | 5/1967 | Sokolik |
| 3,568,659 A | 3/1971 | Karnegis |
| 3,667,476 A | 6/1972 | Muller |

(Continued)

FOREIGN PATENT DOCUMENTS

| | | |
|---|---|---|
| CA | 2419228 | 8/2004 |
| CN | 101115448 | 1/2008 |

(Continued)

OTHER PUBLICATIONS

An, S. S. et al., Airway smooth muscle dynamics; a common pathway of airway obstruction in asthma, European Respiratory Journal, 2007, vol. 29, No. 5, pp. 834-860.

(Continued)

*Primary Examiner* — Nicole F Lavert
(74) *Attorney, Agent, or Firm* — Patterson Thuente Pedersen, P.A.

(57) ABSTRACT

A method of reducing bronchial constriction in a subject includes delivering energy to create one or more lesions on a main bronchus so as to transect pulmonary nerves sufficiently to reduce bronchial constriction in a lung of the patient distal to the main bronchus.

9 Claims, 11 Drawing Sheets

(56) References Cited

U.S. PATENT DOCUMENTS

| | | |
|---|---|---|
| 3,692,029 A | 9/1972 | Adair |
| 3,918,449 A | 11/1975 | Pistor |
| 3,946,745 A | 3/1976 | Hsiang-Lai et al. |
| 3,949,743 A | 4/1976 | Shanbrom |
| 3,995,617 A | 12/1976 | Watkins et al. |
| 4,078,864 A | 3/1978 | Howell |
| 4,095,602 A | 6/1978 | Leveen |
| 4,116,589 A | 9/1978 | Rishton |
| 4,129,129 A | 12/1978 | Amrine |
| 4,154,246 A | 5/1979 | LeVeen |
| 4,277,168 A | 7/1981 | Oku |
| 4,305,402 A | 12/1981 | Katims |
| 4,351,330 A | 9/1982 | Scarberry |
| 4,461,283 A | 7/1984 | Doi |
| 4,502,490 A | 3/1985 | Evans et al. |
| 4,503,855 A | 3/1985 | Maslanka |
| 4,503,863 A | 3/1985 | Katims |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,573,481 A | 3/1986 | Bullara |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,649,924 A | 3/1987 | Taccardi |
| 4,649,935 A | 3/1987 | Charmillot et al. |
| 4,658,836 A | 4/1987 | Turner |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,322 A | 8/1988 | Charmillot et al. |
| 4,765,959 A | 8/1988 | Fukasawa |
| 4,767,402 A | 8/1988 | Kost et al. |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,808,164 A | 2/1989 | Hess |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,881,542 A | 11/1989 | Schmidt et al. |
| 4,895,557 A | 1/1990 | Moise et al. |
| 4,902,129 A | 2/1990 | Siegmund et al. |
| 4,904,472 A | 2/1990 | Belardinelli et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,945,910 A | 8/1990 | Budyko et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,989,604 A | 2/1991 | Fang |
| 4,991,603 A | 2/1991 | Cohen et al. |
| 4,992,474 A | 2/1991 | Skidmore et al. |
| 5,005,559 A | 4/1991 | Blanco et al. |
| 5,007,908 A | 4/1991 | Rydell |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,054,486 A | 10/1991 | Yamada |
| 5,056,519 A | 10/1991 | Vince |
| 5,056,529 A | 10/1991 | de Groot |
| 5,057,107 A | 10/1991 | Parins et al. |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,107,835 A | 4/1992 | Thomas |
| 5,109,846 A | 5/1992 | Thomas |
| 5,114,423 A | 5/1992 | Kasprzyk et al. |
| 5,116,864 A | 5/1992 | March et al. |
| 5,117,828 A | 6/1992 | Metzger et al. |
| 5,123,413 A | 6/1992 | Hasegawa et al. |
| 5,126,375 A | 6/1992 | Skidmore et al. |
| 5,135,480 A | 8/1992 | Bannon et al. |
| 5,135,517 A | 8/1992 | McCoy |
| 5,139,029 A | 8/1992 | Fishman et al. |
| 5,151,100 A | 9/1992 | Abele et al. |
| 5,152,286 A | 10/1992 | Sitko et al. |
| 5,165,420 A | 11/1992 | Strickland |
| 5,167,223 A | 12/1992 | Koros et al. |
| 5,170,802 A | 12/1992 | Mehra |
| 5,170,803 A | 12/1992 | Hewson et al. |
| 5,174,288 A | 12/1992 | Bardy et al. |
| 5,188,602 A | 2/1993 | Nichols |
| 5,190,540 A | 3/1993 | Lee |
| 5,191,883 A | 3/1993 | Lennox et al. |
| 5,213,576 A | 5/1993 | Abiuso et al. |
| 5,215,103 A | 6/1993 | Desai |
| 5,224,491 A | 7/1993 | Mehra |
| 5,225,445 A | 7/1993 | Skidmore et al. |
| 5,231,996 A | 8/1993 | Bardy et al. |
| 5,232,444 A | 8/1993 | Just et al. |
| 5,234,456 A | 8/1993 | Silvestrini |
| 5,239,982 A | 8/1993 | Trauthen |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,286,254 A | 2/1994 | Shapland et al. |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,255 A | 6/1994 | Passafaro et al. |
| 5,324,284 A | 6/1994 | Imran |
| 5,343,936 A | 9/1994 | Beatenbough et al. |
| 5,344,398 A | 9/1994 | Hara |
| 5,345,936 A | 9/1994 | Pomeranz et al. |
| 5,348,554 A | 9/1994 | Imran et al. |
| 5,366,443 A | 11/1994 | Eggers et al. |
| 5,368,591 A | 11/1994 | Lennox et al. |
| 5,370,644 A | 12/1994 | Langberg |
| 5,370,675 A | 12/1994 | Edwards et al. |
| 5,370,679 A | 12/1994 | Atlee, III |
| 5,372,603 A | 12/1994 | Acker et al. |
| 5,374,287 A | 12/1994 | Rubin |
| 5,379,765 A | 1/1995 | Kajiwara et al. |
| 5,383,917 A | 1/1995 | Desai et al. |

(56) References Cited

U.S. PATENT DOCUMENTS

| | | |
|---|---|---|
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,405,362 A | 4/1995 | Kramer et al. |
| 5,405,366 A | 4/1995 | Fox et al. |
| 5,411,025 A | 5/1995 | Webster, Jr. |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,454,840 A | 10/1995 | Krakovsky et al. |
| 5,456,667 A | 10/1995 | Ham et al. |
| 5,458,596 A | 10/1995 | Lax et al. |
| 5,465,717 A | 11/1995 | Imran et al. |
| 5,470,352 A | 11/1995 | Rappaport |
| 5,471,982 A | 12/1995 | Edwards et al. |
| 5,474,530 A | 12/1995 | Passafaro et al. |
| 5,478,309 A | 12/1995 | Sweezer et al. |
| 5,478,578 A | 12/1995 | Arnold et al. |
| 5,496,271 A | 3/1996 | Burton et al. |
| 5,496,304 A | 3/1996 | Chasan |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sitko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,540,730 A | 7/1996 | Terry, Jr. et al. |
| 5,545,161 A | 8/1996 | Imran |
| 5,545,193 A | 8/1996 | Fleischman et al. |
| 5,547,469 A | 8/1996 | Rowland et al. |
| 5,549,559 A | 8/1996 | Eshel |
| 5,549,655 A | 8/1996 | Erickson |
| 5,549,661 A | 8/1996 | Kordis et al. |
| RE35,330 E | 9/1996 | Malone et al. |
| 5,553,611 A | 9/1996 | Budd et al. |
| 5,558,073 A | 9/1996 | Pomeranz et al. |
| 5,562,608 A | 10/1996 | Sekins et al. |
| 5,571,074 A | 11/1996 | Buckman, Jr. et al. |
| 5,571,088 A | 11/1996 | Lennox et al. |
| 5,574,059 A | 11/1996 | Regunathan et al. |
| 5,578,072 A | 11/1996 | Barone et al. |
| 5,582,609 A | 12/1996 | Swanson et al. |
| 5,588,432 A | 12/1996 | Crowley |
| 5,588,812 A | 12/1996 | Taylor et al. |
| 5,595,183 A | 1/1997 | Swanson et al. |
| 5,598,848 A | 2/1997 | Swanson et al. |
| 5,599,345 A | 2/1997 | Edwards et al. |
| 5,601,088 A | 2/1997 | Swanson et al. |
| 5,605,157 A | 2/1997 | Panescu et al. |
| 5,607,419 A | 3/1997 | Amplatz et al. |
| 5,607,462 A | 3/1997 | Imran |
| 5,620,438 A | 4/1997 | Amplatz et al. |
| 5,620,463 A | 4/1997 | Drolet |
| 5,623,940 A | 4/1997 | Daikuzono |
| 5,624,392 A | 4/1997 | Saab |
| 5,624,439 A | 4/1997 | Edwards et al. |
| 5,626,618 A | 5/1997 | Ward et al. |
| 5,627,392 A | 5/1997 | Diorio et al. |
| 5,630,425 A | 5/1997 | Panescu et al. |
| 5,630,794 A | 5/1997 | Lax et al. |
| 5,630,813 A | 5/1997 | Kieturakis |
| 5,634,471 A | 6/1997 | Fairfax et al. |
| 5,641,326 A | 6/1997 | Adams |
| 5,647,870 A | 7/1997 | Kordis et al. |
| 5,658,278 A | 8/1997 | Imran et al. |
| 5,658,322 A | 8/1997 | Fleming |
| 5,658,549 A | 8/1997 | Akehurst et al. |
| 5,660,175 A | 8/1997 | Dayal |
| 5,662,108 A | 9/1997 | Budd et al. |
| 5,669,930 A | 9/1997 | Igarashi |
| 5,669,932 A | 9/1997 | Fischell et al. |
| 5,674,472 A | 10/1997 | Akehurst et al. |
| 5,678,535 A | 10/1997 | DiMarco |
| 5,680,860 A | 10/1997 | Imran |
| 5,681,280 A | 10/1997 | Rusk et al. |
| 5,681,308 A | 10/1997 | Edwards et al. |
| 5,687,723 A | 11/1997 | Avitall |
| 5,688,267 A | 11/1997 | Panescu et al. |
| 5,690,692 A | 11/1997 | Fleming |
| 5,693,078 A | 12/1997 | Desai et al. |
| 5,694,934 A | 12/1997 | Edelman |
| 5,695,471 A | 12/1997 | Wampler |
| 5,699,799 A | 12/1997 | Xu et al. |
| 5,702,386 A | 12/1997 | Stern et al. |
| 5,707,218 A | 1/1998 | Maher et al. |
| 5,707,336 A | 1/1998 | Rubin |
| 5,707,352 A | 1/1998 | Sekins et al. |
| 5,707,400 A | 1/1998 | Terry, Jr. et al. |
| 5,722,401 A | 3/1998 | Pietroski et al. |
| 5,722,403 A | 3/1998 | McGee et al. |
| 5,722,416 A | 3/1998 | Swanson et al. |
| 5,725,525 A | 3/1998 | Kordis |
| 5,727,569 A | 3/1998 | Benetti et al. |
| 5,728,094 A | 3/1998 | Edwards |
| 5,730,128 A | 3/1998 | Pomeranz et al. |
| 5,730,704 A | 3/1998 | Avitall |
| 5,730,726 A | 3/1998 | Klingenstein |
| 5,730,741 A | 3/1998 | Horzewski et al. |
| 5,733,319 A | 3/1998 | Neilson et al. |
| 5,735,846 A | 4/1998 | Panescu et al. |
| 5,740,808 A | 4/1998 | Panescu et al. |
| 5,741,248 A | 4/1998 | Stern et al. |
| 5,746,224 A | 5/1998 | Edwards |
| 5,752,518 A | 5/1998 | McGee et al. |
| 5,755,714 A | 5/1998 | Murphy-Chutorian |
| 5,755,753 A | 5/1998 | Knowlton |
| 5,759,158 A | 6/1998 | Swanson |
| 5,765,568 A | 6/1998 | Sweezer, Jr. et al. |
| 5,766,605 A | 6/1998 | Sanders et al. |
| 5,769,846 A | 6/1998 | Edwards et al. |
| 5,772,590 A | 6/1998 | Webster, Jr. |
| 5,779,669 A | 7/1998 | Haissaguerre et al. |
| 5,779,698 A | 7/1998 | Clayman et al. |
| 5,782,239 A | 7/1998 | Webster, Jr. |
| 5,782,797 A | 7/1998 | Schweich, Jr. et al. |
| 5,782,827 A | 7/1998 | Gough et al. |
| 5,782,848 A | 7/1998 | Lennox |
| 5,782,899 A | 7/1998 | Imran |
| 5,792,064 A | 8/1998 | Panescu et al. |
| 5,795,303 A | 8/1998 | Swanson et al. |
| 5,800,375 A | 9/1998 | Sweezer et al. |
| 5,800,486 A | 9/1998 | Thome et al. |
| 5,807,306 A | 9/1998 | Shapland et al. |
| 5,810,757 A | 9/1998 | Sweezer, Jr. et al. |
| 5,810,807 A | 9/1998 | Ganz et al. |
| 5,814,078 A | 9/1998 | Zhou et al. |
| 5,817,028 A | 10/1998 | Anderson |
| 5,817,073 A | 10/1998 | Krespi |
| 5,820,554 A | 10/1998 | Davis et al. |
| 5,820,589 A | 10/1998 | Torgerson et al. |
| 5,823,189 A | 10/1998 | Kordis |
| 5,827,277 A | 10/1998 | Edwards |
| 5,833,651 A | 11/1998 | Donovan et al. |
| 5,836,874 A | 11/1998 | Swanson et al. |
| 5,836,905 A | 11/1998 | Lemelson et al. |
| 5,836,947 A | 11/1998 | Fleischman et al. |
| 5,837,001 A | 11/1998 | Mackey |

(56) References Cited

U.S. PATENT DOCUMENTS

| | | |
|---|---|---|
| 5,843,075 A | 12/1998 | Taylor |
| 5,843,077 A | 12/1998 | Edwards |
| 5,843,088 A | 12/1998 | Barra et al. |
| 5,846,238 A | 12/1998 | Jackson et al. |
| 5,848,969 A | 12/1998 | Panescu et al. |
| 5,848,972 A | 12/1998 | Triedman et al. |
| 5,849,026 A | 12/1998 | Zhou et al. |
| 5,855,577 A | 1/1999 | Murphy-Chutorian et al. |
| 5,860,974 A | 1/1999 | Abele |
| 5,863,291 A | 1/1999 | Schaer |
| 5,865,791 A | 2/1999 | Whayne et al. |
| 5,868,740 A | 2/1999 | LeVeen et al. |
| 5,871,443 A | 2/1999 | Edwards et al. |
| 5,871,483 A | 2/1999 | Jackson et al. |
| 5,871,523 A | 2/1999 | Fleischman et al. |
| 5,873,852 A | 2/1999 | Vigil et al. |
| 5,873,865 A | 2/1999 | Horzewski et al. |
| 5,876,340 A | 3/1999 | Tu et al. |
| 5,876,399 A | 3/1999 | Chia et al. |
| 5,881,727 A | 3/1999 | Edwards |
| 5,882,346 A | 3/1999 | Pomeranz et al. |
| 5,891,027 A | 4/1999 | Tu et al. |
| 5,891,135 A | 4/1999 | Jackson et al. |
| 5,891,136 A | 4/1999 | McGee et al. |
| 5,891,138 A | 4/1999 | Tu et al. |
| 5,891,182 A | 4/1999 | Fleming |
| 5,893,847 A | 4/1999 | Kordis |
| 5,893,887 A | 4/1999 | Jayaraman |
| 5,897,554 A | 4/1999 | Chia et al. |
| 5,899,882 A | 5/1999 | Waksman et al. |
| 5,902,268 A | 5/1999 | Saab |
| 5,904,651 A | 5/1999 | Swanson et al. |
| 5,904,711 A | 5/1999 | Flom et al. |
| 5,906,636 A | 5/1999 | Casscells, III et al. |
| 5,908,445 A | 6/1999 | Whayne et al. |
| 5,908,446 A | 6/1999 | Imran |
| 5,908,839 A | 6/1999 | Levitt et al. |
| 5,911,218 A | 6/1999 | DiMarco |
| 5,916,235 A | 6/1999 | Guglielmi |
| 5,919,147 A | 7/1999 | Jain |
| 5,919,172 A | 7/1999 | Golba, Jr. |
| 5,924,424 A | 7/1999 | Stevens et al. |
| 5,928,228 A | 7/1999 | Kordis et al. |
| 5,931,806 A | 8/1999 | Shimada |
| 5,931,835 A | 8/1999 | Mackey |
| 5,935,079 A | 8/1999 | Swanson et al. |
| 5,941,869 A | 8/1999 | Patterson et al. |
| 5,951,494 A | 9/1999 | Wang et al. |
| 5,951,546 A | 9/1999 | Lorentzen |
| 5,954,661 A | 9/1999 | Greenspan et al. |
| 5,954,662 A | 9/1999 | Swanson et al. |
| 5,954,717 A | 9/1999 | Behl et al. |
| 5,956,501 A | 9/1999 | Brown |
| 5,957,919 A | 9/1999 | Laufer |
| 5,957,961 A | 9/1999 | Maguire et al. |
| 5,964,223 A | 10/1999 | Baran |
| 5,964,753 A | 10/1999 | Edwards |
| 5,964,796 A | 10/1999 | Imran |
| 5,971,983 A | 10/1999 | Lesh |
| 5,972,026 A | 10/1999 | Laufer et al. |
| 5,976,175 A | 11/1999 | Hirano et al. |
| 5,976,709 A | 11/1999 | Kageyama et al. |
| 5,979,456 A | 11/1999 | Magovern |
| 5,980,563 A | 11/1999 | Tu et al. |
| 5,984,917 A | 11/1999 | Fleischman et al. |
| 5,984,971 A | 11/1999 | Faccioli et al. |
| 5,989,545 A | 11/1999 | Foster et al. |
| 5,991,650 A | 11/1999 | Swanson et al. |
| 5,992,419 A | 11/1999 | Sterzer et al. |
| 5,993,462 A | 11/1999 | Pomeranz et al. |
| 5,995,873 A | 11/1999 | Rhodes |
| 5,997,534 A | 12/1999 | Tu et al. |
| 5,999,855 A | 12/1999 | DiMarco |
| 6,001,054 A | 12/1999 | Regulla et al. |
| 6,003,517 A | 12/1999 | Sheffield et al. |
| 6,004,269 A | 12/1999 | Crowley et al. |
| 6,006,134 A | 12/1999 | Hill et al. |
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,043,273 A | 3/2000 | Duhaylongsod |
| 6,045,549 A | 4/2000 | Smethers et al. |
| 6,045,550 A | 4/2000 | Simpson et al. |
| 6,050,992 A | 4/2000 | Nichols |
| 6,052,607 A | 4/2000 | Edwards et al. |
| 6,053,172 A | 4/2000 | Hovda et al. |
| 6,053,909 A | 4/2000 | Shadduck |
| 6,056,744 A | 5/2000 | Edwards |
| 6,056,745 A | 5/2000 | Panescu et al. |
| 6,056,769 A | 5/2000 | Epstein et al. |
| 6,060,454 A | 5/2000 | Duhaylongsod |
| 6,063,078 A | 5/2000 | Wittkampf |
| 6,063,768 A | 5/2000 | First |
| 6,071,280 A | 6/2000 | Edwards et al. |
| 6,071,281 A | 6/2000 | Burnside et al. |
| 6,071,282 A | 6/2000 | Fleischman |
| 6,081,749 A | 6/2000 | Ingle et al. |
| 6,083,249 A | 7/2000 | Familoni |
| 6,083,255 A | 7/2000 | Laufer et al. |
| 6,087,394 A | 7/2000 | Duhaylongsod |
| 6,090,104 A | 7/2000 | Webster, Jr. |
| 6,091,995 A | 7/2000 | Ingle et al. |
| 6,092,528 A | 7/2000 | Edwards |
| 6,097,985 A | 8/2000 | Kasevich et al. |
| 6,101,412 A | 8/2000 | Duhaylongsod |
| 6,102,886 A | 8/2000 | Lundquist et al. |
| 6,106,524 A | 8/2000 | Eggers et al. |
| 6,117,101 A | 9/2000 | Diederich et al. |
| 6,123,702 A | 9/2000 | Swanson et al. |
| 6,123,703 A | 9/2000 | Tu et al. |
| 6,123,718 A | 9/2000 | Tu et al. |
| 6,125,301 A | 9/2000 | Capel |
| 6,127,410 A | 10/2000 | Duhaylongsod |
| 6,129,726 A | 10/2000 | Edwards et al. |
| 6,135,997 A | 10/2000 | Laufer et al. |
| 6,139,527 A | 10/2000 | Laufer et al. |
| 6,139,571 A | 10/2000 | Fuller et al. |
| 6,139,845 A | 10/2000 | Donovan |
| 6,141,589 A | 10/2000 | Duhaylongsod |
| 6,142,993 A | 11/2000 | Whayne et al. |
| 6,143,013 A | 11/2000 | Samson et al. |
| 6,143,277 A | 11/2000 | Ashurst et al. |
| 6,149,647 A | 11/2000 | Tu et al. |
| 6,152,143 A | 11/2000 | Edwards |
| 6,152,899 A | 11/2000 | Farley et al. |
| 6,152,953 A | 11/2000 | Hipskind |
| 6,159,194 A | 12/2000 | Eggers et al. |
| 6,163,716 A | 12/2000 | Edwards et al. |
| 6,174,323 B1 | 1/2001 | Biggs et al. |
| 6,179,833 B1 | 1/2001 | Taylor |
| 6,183,468 B1 | 2/2001 | Swanson et al. |
| 6,197,013 B1 | 3/2001 | Reed et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,203,562 B1 | 3/2001 | Ohkubo |
| 6,210,367 B1 | 4/2001 | Carr |
| 6,212,432 B1 | 4/2001 | Matsuura |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,216,704 B1 | 4/2001 | Ingle et al. |

(56) References Cited

U.S. PATENT DOCUMENTS

| | | |
|---|---|---|
| 6,217,576 B1 | 4/2001 | Tu et al. |
| 6,226,543 B1 | 5/2001 | Gilboa et al. |
| 6,230,052 B1 | 5/2001 | Wolff et al. |
| 6,231,595 B1 | 5/2001 | Dobak, III |
| 6,235,024 B1 | 5/2001 | Tu |
| 6,240,307 B1 | 5/2001 | Beatty et al. |
| 6,241,727 B1 | 6/2001 | Tu et al. |
| 6,245,065 B1 | 6/2001 | Panescu et al. |
| 6,251,368 B1 | 6/2001 | Akehurst et al. |
| 6,253,762 B1 | 7/2001 | Britto |
| 6,254,598 B1 | 7/2001 | Edwards et al. |
| 6,254,599 B1 | 7/2001 | Lesh et al. |
| 6,258,083 B1 | 7/2001 | Daniel et al. |
| 6,258,087 B1 | 7/2001 | Edwards et al. |
| 6,264,653 B1 | 7/2001 | Falwell |
| 6,265,379 B1 | 7/2001 | Donovan |
| 6,269,813 B1 | 8/2001 | Fitzgerald et al. |
| 6,270,476 B1 | 8/2001 | Santoianni et al. |
| 6,273,886 B1 | 8/2001 | Edwards et al. |
| 6,273,907 B1 | 8/2001 | Laufer |
| 6,283,987 B1 | 9/2001 | Laird et al. |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,299,633 B1 | 10/2001 | Laufer |
| 6,302,870 B1 | 10/2001 | Jacobsen et al. |
| 6,303,509 B1 | 10/2001 | Chen et al. |
| 6,306,423 B1 | 10/2001 | Donovan et al. |
| 6,315,173 B1 | 11/2001 | Di Giovanni et al. |
| 6,315,778 B1 | 11/2001 | Gambale et al. |
| 6,317,615 B1 | 11/2001 | KenKnight et al. |
| 6,322,559 B1 | 11/2001 | Daulton et al. |
| 6,322,584 B2 | 11/2001 | Ingle et al. |
| 6,325,798 B1 | 12/2001 | Edwards et al. |
| 6,327,503 B1 | 12/2001 | Familoni |
| 6,338,727 B1 | 1/2002 | Noda et al. |
| 6,338,836 B1 | 1/2002 | Kuth et al. |
| 6,341,236 B1 | 1/2002 | Osorio et al. |
| 6,346,104 B2 | 2/2002 | Daly et al. |
| 6,355,031 B1 | 3/2002 | Edwards et al. |
| 6,356,786 B1 | 3/2002 | Rezai et al. |
| 6,356,787 B1 | 3/2002 | Rezai et al. |
| 6,357,447 B1 | 3/2002 | Swanson et al. |
| 6,358,245 B1 | 3/2002 | Edwards et al. |
| 6,358,926 B2 | 3/2002 | Donovan |
| 6,361,554 B1 | 3/2002 | Brisken |
| 6,363,937 B1 | 4/2002 | Hovda et al. |
| 6,366,814 B1 | 4/2002 | Boveja et al. |
| 6,379,352 B1 | 4/2002 | Reynolds et al. |
| 6,383,509 B1 | 5/2002 | Donovan et al. |
| 6,394,956 B1 | 5/2002 | Chandrasekaran et al. |
| 6,402,744 B2 | 6/2002 | Edwards et al. |
| 6,405,732 B1 | 6/2002 | Edwards et al. |
| 6,409,723 B1 | 6/2002 | Edwards |
| 6,411,852 B1 | 6/2002 | Danek et al. |
| 6,414,018 B1 | 7/2002 | Duhaylongsod |
| 6,416,511 B1 | 7/2002 | Lesh et al. |
| 6,416,740 B1 | 7/2002 | Unger |
| 6,423,058 B1 | 7/2002 | Edwards et al. |
| 6,423,105 B1 | 7/2002 | Iijima et al. |
| 6,424,864 B1 | 7/2002 | Matsuura |
| 6,425,877 B1 | 7/2002 | Edwards |
| 6,425,887 B1 | 7/2002 | McGuckin et al. |
| 6,425,895 B1 | 7/2002 | Swanson et al. |
| 6,432,092 B2 | 8/2002 | Miller |
| 6,436,130 B1 | 8/2002 | Philips et al. |
| 6,438,423 B1 | 8/2002 | Rezai et al. |
| 6,440,128 B1 | 8/2002 | Edwards et al. |
| 6,440,129 B1 | 8/2002 | Simpson |
| 6,442,435 B2 | 8/2002 | King et al. |
| 6,447,505 B2 | 9/2002 | McGovern et al. |
| 6,447,785 B1 | 9/2002 | Donovan |
| 6,448,231 B2 | 9/2002 | Graham |
| 6,458,121 B1 | 10/2002 | Rosenstock et al. |
| 6,460,545 B2 | 10/2002 | Kordis |
| 6,464,680 B1 | 10/2002 | Brisken et al. |
| 6,464,697 B1 | 10/2002 | Edwards et al. |
| 6,475,160 B1 | 11/2002 | Sher |
| 6,480,746 B1 | 11/2002 | Ingle et al. |
| 6,485,416 B1 | 11/2002 | Platt et al. |
| 6,488,673 B1 | 12/2002 | Laufer et al. |
| 6,488,679 B1 | 12/2002 | Swanson et al. |
| 6,491,710 B2 | 12/2002 | Satake |
| 6,493,589 B1 | 12/2002 | Medhkour et al. |
| 6,494,880 B1 | 12/2002 | Swanson et al. |
| 6,496,737 B2 | 12/2002 | Rudie et al. |
| 6,496,738 B2 | 12/2002 | Carr |
| 6,506,399 B2 | 1/2003 | Donovan |
| 6,510,969 B2 | 1/2003 | Di Giovanni et al. |
| 6,514,246 B1 | 2/2003 | Swanson et al. |
| 6,514,290 B1 | 2/2003 | Loomas |
| 6,519,488 B2 | 2/2003 | KenKnight et al. |
| 6,522,913 B2 | 2/2003 | Swanson et al. |
| 6,524,555 B1 | 2/2003 | Ashurst et al. |
| 6,526,320 B2 | 2/2003 | Mitchell |
| 6,526,976 B1 | 3/2003 | Baran |
| 6,529,756 B1 | 3/2003 | Phan et al. |
| 6,532,388 B1 | 3/2003 | Hill et al. |
| 6,533,780 B1 | 3/2003 | Laird et al. |
| 6,536,427 B2 | 3/2003 | Davies et al. |
| 6,544,226 B1 | 4/2003 | Gaiser et al. |
| 6,544,262 B2 | 4/2003 | Fleischman |
| 6,546,928 B1 | 4/2003 | Ashurst et al. |
| 6,546,932 B1 | 4/2003 | Nahon et al. |
| 6,546,934 B1 | 4/2003 | Ingle et al. |
| 6,547,776 B1 | 4/2003 | Gaiser et al. |
| 6,547,788 B1 | 4/2003 | Maguire et al. |
| 6,549,808 B1 | 4/2003 | Gisel et al. |
| 6,551,274 B2 | 4/2003 | Heiner |
| 6,551,310 B1 | 4/2003 | Ganz et al. |
| 6,558,333 B2 | 5/2003 | Gilboa et al. |
| 6,558,378 B2 | 5/2003 | Sherman et al. |
| 6,558,381 B2 | 5/2003 | Ingle et al. |
| 6,562,034 B2 | 5/2003 | Edwards et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,587,718 B2 | 7/2003 | Talpade |
| 6,587,719 B1 | 7/2003 | Barrett et al. |
| 6,587,731 B1 | 7/2003 | Ingle et al. |
| 6,589,235 B2 | 7/2003 | Wong et al. |
| 6,589,238 B2 | 7/2003 | Edwards et al. |
| 6,593,130 B1 | 7/2003 | Sen et al. |
| 6,599,311 B1 | 7/2003 | Biggs et al. |
| 6,601,581 B1 | 8/2003 | Babaev |
| 6,603,996 B1 | 8/2003 | Beatty et al. |
| 6,610,054 B1 | 8/2003 | Edwards et al. |
| 6,610,083 B2 | 8/2003 | Keller et al. |
| 6,610,713 B2 | 8/2003 | Tracey |
| 6,613,002 B1 | 9/2003 | Clark et al. |
| 6,613,045 B1 | 9/2003 | Laufer et al. |
| 6,620,159 B2 | 9/2003 | Hegde |
| 6,620,415 B2 | 9/2003 | Donovan |
| 6,622,047 B2 | 9/2003 | Barrett et al. |
| 6,623,742 B2 | 9/2003 | Voet |
| 6,626,855 B1 | 9/2003 | Weng et al. |
| 6,626,903 B2 | 9/2003 | McGuckin, Jr. et al. |
| 6,629,535 B2 | 10/2003 | Ingle et al. |
| 6,629,951 B2 | 10/2003 | Laufer et al. |
| 6,632,440 B1 | 10/2003 | Quinn et al. |
| 6,633,779 B1 | 10/2003 | Schuler et al. |
| 6,634,363 B1 | 10/2003 | Danek et al. |
| 6,635,054 B2 | 10/2003 | Fjield et al. |
| 6,635,056 B2 | 10/2003 | Kadhiresan et al. |
| 6,638,273 B1 | 10/2003 | Farley et al. |
| 6,640,119 B1 | 10/2003 | Budd et al. |
| 6,640,120 B1 | 10/2003 | Swanson et al. |
| 6,645,200 B1 | 11/2003 | Koblish et al. |
| 6,645,496 B2 | 11/2003 | Aoki et al. |
| 6,647,617 B1 | 11/2003 | Beatty et al. |
| 6,648,881 B2 | 11/2003 | KenKnight et al. |

(56) References Cited

U.S. PATENT DOCUMENTS

| | | |
|---|---|---|
| 6,649,161 B1 | 11/2003 | Donovan |
| 6,652,517 B1 | 11/2003 | Hall et al. |
| 6,652,548 B2 | 11/2003 | Evans et al. |
| 6,656,960 B2 | 12/2003 | Puskas |
| 6,658,279 B2 | 12/2003 | Swanson et al. |
| 6,663,622 B1 | 12/2003 | Foley et al. |
| 6,666,858 B2 | 12/2003 | Lafontaine |
| 6,669,693 B2 | 12/2003 | Friedman |
| 6,673,068 B1 | 1/2004 | Berube |
| 6,673,070 B2 | 1/2004 | Edwards et al. |
| 6,675,047 B1 | 1/2004 | Konoplev et al. |
| 6,676,686 B2 | 1/2004 | Naganuma |
| 6,681,136 B2 | 1/2004 | Schuler et al. |
| 6,692,492 B2 | 2/2004 | Simpson et al. |
| 6,692,494 B1 | 2/2004 | Cooper et al. |
| 6,699,180 B2 | 3/2004 | Kobayashi |
| 6,699,243 B2 | 3/2004 | West et al. |
| 6,708,064 B2 | 3/2004 | Rezai |
| 6,711,436 B1 | 3/2004 | Duhaylongsod |
| 6,712,074 B2 | 3/2004 | Edwards et al. |
| 6,712,812 B2 | 3/2004 | Roschak et al. |
| 6,712,814 B2 | 3/2004 | Edwards et al. |
| 6,714,822 B2 | 3/2004 | King et al. |
| 6,719,685 B2 | 4/2004 | Fujikura et al. |
| 6,719,694 B2 | 4/2004 | Weng et al. |
| 6,723,053 B2 | 4/2004 | Ackerman et al. |
| 6,723,091 B2 | 4/2004 | Goble et al. |
| 6,728,562 B1 | 4/2004 | Budd et al. |
| 6,735,471 B2 | 5/2004 | Hill et al. |
| 6,735,475 B1 | 5/2004 | Whitehurst et al. |
| 6,740,321 B1 | 5/2004 | Donovan |
| 6,743,197 B1 | 6/2004 | Edwards |
| 6,743,413 B1 | 6/2004 | Schultz et al. |
| 6,749,604 B1 | 6/2004 | Eggers et al. |
| 6,749,606 B2 | 6/2004 | Keast et al. |
| 6,752,765 B1 | 6/2004 | Jensen et al. |
| 6,755,026 B2 | 6/2004 | Wallach |
| 6,755,849 B1 | 6/2004 | Gowda et al. |
| 6,767,347 B2 | 7/2004 | Sharkey et al. |
| 6,767,544 B2 | 7/2004 | Brooks et al. |
| 6,770,070 B1 | 8/2004 | Balbierz |
| 6,772,013 B1 | 8/2004 | Ingle et al. |
| 6,773,711 B2 | 8/2004 | Voet et al. |
| 6,776,991 B2 | 8/2004 | Naumann |
| 6,777,423 B2 | 8/2004 | Banholzer et al. |
| 6,778,854 B2 | 8/2004 | Puskas |
| 6,780,183 B2 | 8/2004 | Jimenez et al. |
| 6,786,889 B1 | 9/2004 | Musbach et al. |
| 6,802,843 B2 | 10/2004 | Truckai et al. |
| 6,805,131 B2 | 10/2004 | Kordis |
| 6,819,956 B2 | 11/2004 | DiLorenzo |
| 6,826,420 B1 | 11/2004 | Beatty et al. |
| 6,826,421 B1 | 11/2004 | Beatty et al. |
| 6,827,931 B1 | 12/2004 | Donovan |
| 6,836,688 B2 | 12/2004 | Ingle et al. |
| 6,837,888 B2 | 1/2005 | Ciarrocca et al. |
| 6,838,429 B2 | 1/2005 | Paslin |
| 6,838,434 B2 | 1/2005 | Voet |
| 6,838,471 B2 | 1/2005 | Tracey |
| 6,840,243 B2 | 1/2005 | Deem et al. |
| 6,841,156 B2 | 1/2005 | Aoki et al. |
| 6,843,998 B1 | 1/2005 | Steward et al. |
| 6,846,312 B2 | 1/2005 | Edwards et al. |
| 6,847,849 B2 | 1/2005 | Mamo et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,861,058 B2 | 3/2005 | Aoki et al. |
| 6,866,662 B2 | 3/2005 | Fuimaono et al. |
| 6,871,092 B2 | 3/2005 | Piccone |
| 6,872,206 B2 | 3/2005 | Edwards et al. |
| 6,872,397 B2 | 3/2005 | Aoki et al. |
| 6,878,156 B1 | 4/2005 | Noda |
| 6,881,213 B2 | 4/2005 | Ryan et al. |
| 6,885,888 B2 | 4/2005 | Rezai |
| 6,890,347 B2 | 5/2005 | Machold et al. |
| 6,893,436 B2 | 5/2005 | Woodard et al. |
| 6,893,438 B2 | 5/2005 | Hall et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,908,462 B2 | 6/2005 | Joye et al. |
| 6,908,928 B2 | 6/2005 | Banholzer et al. |
| 6,913,616 B2 | 7/2005 | Hamilton et al. |
| 6,917,834 B2 | 7/2005 | Koblish et al. |
| 6,934,583 B2 | 8/2005 | Weinberg et al. |
| 6,937,896 B1 | 8/2005 | Kroll |
| 6,937,903 B2 | 8/2005 | Schuler et al. |
| 6,939,309 B1 | 9/2005 | Beatty et al. |
| 6,939,345 B2 | 9/2005 | KenKnight et al. |
| 6,939,346 B2 | 9/2005 | Kannenberg et al. |
| 6,947,785 B1 | 9/2005 | Beatty et al. |
| 6,954,977 B2 | 10/2005 | Maguire et al. |
| 6,957,106 B2 | 10/2005 | Schuler et al. |
| 6,961,622 B2 | 11/2005 | Gilbert |
| 6,970,742 B2 | 11/2005 | Mann et al. |
| RE38,912 E | 12/2005 | Walz et al. |
| 6,971,395 B2 | 12/2005 | Edwards et al. |
| 6,974,224 B2 | 12/2005 | Thomas-Benedict |
| 6,974,456 B2 | 12/2005 | Edwards et al. |
| 6,974,578 B1 | 12/2005 | Aoki et al. |
| 6,978,168 B2 | 12/2005 | Beatty et al. |
| 6,978,174 B2 | 12/2005 | Gelfand et al. |
| 6,990,370 B1 | 1/2006 | Beatty et al. |
| 6,994,706 B2 | 2/2006 | Chornenky et al. |
| 6,997,189 B2 | 2/2006 | Biggs et al. |
| 7,004,942 B2 | 2/2006 | Laird et al. |
| 7,022,088 B2 | 4/2006 | Keast et al. |
| 7,022,105 B1 | 4/2006 | Edwards |
| 7,027,869 B2 | 4/2006 | Danek et al. |
| 7,043,307 B1 | 5/2006 | Zelickson et al. |
| 7,070,800 B2 | 7/2006 | Bechtold-Peters et al. |
| 7,072,720 B2 | 7/2006 | Puskas |
| 7,083,614 B2 | 8/2006 | Fjield et al. |
| 7,101,368 B2 | 9/2006 | Lafontaine |
| 7,101,387 B2 | 9/2006 | Garabedian et al. |
| 7,104,987 B2 | 9/2006 | Biggs et al. |
| 7,104,990 B2 | 9/2006 | Jenkins et al. |
| 7,112,198 B2 | 9/2006 | Satake |
| 7,118,568 B2 | 10/2006 | Hassett et al. |
| 7,122,031 B2 | 10/2006 | Edwards et al. |
| 7,122,033 B2 | 10/2006 | Wood |
| 7,125,407 B2 | 10/2006 | Edwards et al. |
| 7,131,445 B2 | 11/2006 | Amoah |
| 7,142,910 B2 | 11/2006 | Puskas |
| 7,150,745 B2 | 12/2006 | Stern et al. |
| 7,162,303 B2 | 1/2007 | Levin et al. |
| 7,165,551 B2 | 1/2007 | Edwards et al. |
| 7,167,757 B2 | 1/2007 | Ingle et al. |
| 7,175,644 B2 | 2/2007 | Cooper et al. |
| 7,179,257 B2 | 2/2007 | West et al. |
| 7,186,251 B2 | 3/2007 | Malecki et al. |
| 7,187,964 B2 | 3/2007 | Khoury |
| 7,187,973 B2 | 3/2007 | Hauck |
| 7,189,208 B1 | 3/2007 | Beatty et al. |
| 7,198,635 B2 | 4/2007 | Danek et al. |
| 7,200,445 B1 | 4/2007 | Dalbec et al. |
| 7,229,469 B1 | 6/2007 | Witzel et al. |
| 7,238,357 B2 | 7/2007 | Barron |
| 7,241,295 B2 | 7/2007 | Maguire |
| 7,255,693 B1 | 8/2007 | Johnston et al. |
| RE39,820 E | 9/2007 | Banholzer et al. |
| 7,264,002 B2 | 9/2007 | Danek et al. |
| 7,266,414 B2 | 9/2007 | Cornelius et al. |
| 7,273,055 B2 | 9/2007 | Danek et al. |
| 7,289,843 B2 | 10/2007 | Beatty et al. |
| 7,291,146 B2 | 11/2007 | Steinke et al. |
| 7,292,890 B2 | 11/2007 | Whitehurst et al. |
| 7,309,707 B2 | 12/2007 | Bender et al. |
| 7,310,552 B2 | 12/2007 | Puskas |
| RE40,045 E | 2/2008 | Palmer |
| 7,326,207 B2 | 2/2008 | Edwards |
| 7,344,535 B2 | 3/2008 | Stern et al. |
| 7,371,231 B2 | 5/2008 | Rioux et al. |

(56) References Cited

U.S. PATENT DOCUMENTS

| | | |
|---|---|---|
| 7,393,330 B2 | 7/2008 | Keast et al. |
| 7,393,350 B2 | 7/2008 | Maurice |
| 7,394,976 B2 | 7/2008 | Entenman et al. |
| 7,402,172 B2 | 7/2008 | Chin et al. |
| 7,422,563 B2 | 9/2008 | Roschak et al. |
| 7,422,584 B2 | 9/2008 | Loomas et al. |
| 7,425,212 B1 | 9/2008 | Danek et al. |
| 7,430,449 B2 | 9/2008 | Aldrich et al. |
| 7,462,162 B2 | 12/2008 | Phan et al. |
| 7,462,179 B2 | 12/2008 | Edwards et al. |
| 7,473,273 B2 | 1/2009 | Campbell |
| 7,477,945 B2 | 1/2009 | Rezai et al. |
| 7,483,755 B2 | 1/2009 | Ingle et al. |
| 7,493,160 B2 | 2/2009 | Weber et al. |
| 7,494,661 B2 | 2/2009 | Sanders |
| 7,507,234 B2 | 3/2009 | Utley et al. |
| 7,507,238 B2 | 3/2009 | Edwards et al. |
| 7,517,320 B2 | 4/2009 | Wibowo et al. |
| 7,530,979 B2 | 5/2009 | Ganz et al. |
| 7,532,938 B2 | 5/2009 | Machado et al. |
| 7,542,802 B2 | 6/2009 | Danek et al. |
| 7,553,307 B2 | 6/2009 | Bleich et al. |
| 7,556,624 B2 | 7/2009 | Laufer et al. |
| 7,559,890 B2 | 7/2009 | Wallace et al. |
| 7,572,245 B2 | 8/2009 | Herweck et al. |
| 7,585,296 B2 | 9/2009 | Edwards et al. |
| 7,588,549 B2 | 9/2009 | Eccleston |
| 7,594,925 B2 | 9/2009 | Danek et al. |
| 7,608,275 B2 | 10/2009 | Deem et al. |
| 7,613,515 B2 | 11/2009 | Knudson et al. |
| 7,617,005 B2 | 11/2009 | Demarais et al. |
| 7,620,451 B2 | 11/2009 | Demarais et al. |
| 7,628,789 B2 | 12/2009 | Soltesz et al. |
| 7,632,268 B2 | 12/2009 | Edwards et al. |
| 7,641,632 B2 | 1/2010 | Noda et al. |
| 7,641,633 B2 | 1/2010 | Laufer et al. |
| 7,648,500 B2 | 1/2010 | Edwards et al. |
| 7,653,438 B2 | 1/2010 | Deem et al. |
| 7,684,865 B2 | 3/2010 | Aldrich et al. |
| 7,689,290 B2 | 3/2010 | Ingle et al. |
| 7,691,079 B2 | 4/2010 | Gobel |
| RE41,334 E | 5/2010 | Beatty et al. |
| 7,708,712 B2 | 5/2010 | Phan et al. |
| 7,708,768 B2 | 5/2010 | Danek et al. |
| 7,711,430 B2 | 5/2010 | Errico et al. |
| 7,717,948 B2 | 5/2010 | Demarais et al. |
| 7,722,538 B2 | 5/2010 | Khoury |
| 7,725,188 B2 | 5/2010 | Errico et al. |
| 7,734,355 B2 | 6/2010 | Cohen et al. |
| 7,734,535 B1 | 6/2010 | Burns |
| 7,740,017 B2 | 6/2010 | Danek et al. |
| 7,740,631 B2 | 6/2010 | Bleich et al. |
| 7,742,795 B2 | 6/2010 | Stone et al. |
| 7,747,324 B2 | 6/2010 | Errico et al. |
| 7,756,583 B2 | 7/2010 | Demarais et al. |
| 7,765,010 B2 | 7/2010 | Chornenky et al. |
| 7,770,584 B2 | 8/2010 | Danek et al. |
| 7,783,358 B2 | 8/2010 | Aldrich et al. |
| 7,815,590 B2 | 10/2010 | Cooper |
| 7,826,881 B1 | 11/2010 | Beatty et al. |
| 7,831,288 B1 | 11/2010 | Beatty et al. |
| 7,837,676 B2 | 11/2010 | Sinelnikov et al. |
| 7,837,679 B2 | 11/2010 | Biggs et al. |
| 7,841,986 B2 | 11/2010 | He et al. |
| 7,844,338 B2 | 11/2010 | Knudson et al. |
| 7,853,331 B2 | 12/2010 | Kaplan et al. |
| 7,854,734 B2 | 12/2010 | Biggs et al. |
| 7,854,740 B2 | 12/2010 | Carney |
| 7,869,879 B2 | 1/2011 | Errico et al. |
| 7,869,880 B2 | 1/2011 | Errico et al. |
| 7,873,417 B2 | 1/2011 | Demarais et al. |
| 7,877,146 B2 | 1/2011 | Rezai et al. |
| 7,904,159 B2 | 3/2011 | Errico et al. |
| 7,906,124 B2 | 3/2011 | Laufer et al. |
| 7,914,448 B2 | 3/2011 | Bob et al. |
| 7,921,855 B2 | 4/2011 | Danek et al. |
| 7,930,012 B2 | 4/2011 | Beatty et al. |
| 7,931,647 B2 | 4/2011 | Wizeman et al. |
| 7,937,143 B2 | 5/2011 | Demarais et al. |
| 7,938,123 B2 | 5/2011 | Danek et al. |
| 7,949,407 B2 | 5/2011 | Kaplan et al. |
| 7,967,782 B2 | 6/2011 | Laufer et al. |
| 7,985,187 B2 | 7/2011 | Wibowo et al. |
| 7,992,572 B2 | 8/2011 | Danek et al. |
| 7,993,336 B2 | 8/2011 | Jackson et al. |
| 8,002,740 B2 | 8/2011 | Willink et al. |
| 8,010,197 B2 | 8/2011 | Errico et al. |
| 8,012,149 B2 | 9/2011 | Jackson et al. |
| 8,041,428 B2 | 10/2011 | Errico et al. |
| 8,046,085 B2 | 10/2011 | Knudson et al. |
| 8,052,668 B2 | 11/2011 | Sih |
| 8,088,127 B2 | 1/2012 | Mayse et al. |
| 8,099,167 B1 | 1/2012 | Errico et al. |
| 8,105,817 B2 | 1/2012 | Deem et al. |
| 8,128,595 B2 | 3/2012 | Walker et al. |
| 8,128,617 B2 | 3/2012 | Bencini et al. |
| 8,131,371 B2 | 3/2012 | Demarals et al. |
| 8,152,803 B2 | 4/2012 | Edwards et al. |
| 8,204,598 B2 | 6/2012 | Errico et al. |
| 8,208,998 B2 | 6/2012 | Beatty et al. |
| 8,209,034 B2 | 6/2012 | Simon et al. |
| 8,216,216 B2 | 7/2012 | Warnking et al. |
| 8,226,638 B2 | 7/2012 | Mayse et al. |
| 8,229,564 B2 | 7/2012 | Rezai |
| 8,231,621 B2 | 7/2012 | Hutchins et al. |
| 8,233,988 B2 | 7/2012 | Errico et al. |
| 8,251,992 B2 | 8/2012 | Utley et al. |
| 8,267,094 B2 | 9/2012 | Danek et al. |
| 8,295,902 B2 | 10/2012 | Salahieh et al. |
| 8,303,581 B2 | 11/2012 | Arts et al. |
| 8,313,484 B2 | 11/2012 | Edwards et al. |
| 8,328,798 B2 | 12/2012 | Witzel et al. |
| 8,347,891 B2 | 1/2013 | Demarais et al. |
| 8,357,118 B2 | 1/2013 | Orr |
| 8,364,237 B2 | 1/2013 | Stone et al. |
| 8,371,303 B2 | 2/2013 | Schaner et al. |
| 8,377,055 B2 | 2/2013 | Jackson et al. |
| 8,483,831 B1 | 7/2013 | Hlavka et al. |
| 8,489,192 B1 | 7/2013 | Hlavka et al. |
| 2001/0020151 A1 | 9/2001 | Reed et al. |
| 2001/0044596 A1 | 11/2001 | Jaafar |
| 2002/0002387 A1 | 1/2002 | Naganuma |
| 2002/0010495 A1 | 1/2002 | Freed et al. |
| 2002/0016344 A1 | 2/2002 | Tracey |
| 2002/0042564 A1 | 4/2002 | Cooper et al. |
| 2002/0042565 A1 | 4/2002 | Cooper et al. |
| 2002/0049370 A1 | 4/2002 | Laufer et al. |
| 2002/0072738 A1 | 6/2002 | Edwards et al. |
| 2002/0082197 A1 | 6/2002 | Aoki et al. |
| 2002/0087153 A1 | 7/2002 | Roschak et al. |
| 2002/0087208 A1 | 7/2002 | Koblish et al. |
| 2002/0091379 A1 | 7/2002 | Danek et al. |
| 2002/0107512 A1 | 8/2002 | Edwards |
| 2002/0107515 A1 | 8/2002 | Edwards et al. |
| 2002/0111386 A1 | 8/2002 | Sekins et al. |
| 2002/0111619 A1 | 8/2002 | Keast et al. |
| 2002/0111620 A1 | 8/2002 | Cooper et al. |
| 2002/0115991 A1 | 8/2002 | Edwards |
| 2002/0116030 A1 | 8/2002 | Rezai |
| 2002/0143302 A1 | 10/2002 | Hinchliffe et al. |
| 2002/0143326 A1 | 10/2002 | Foley et al. |
| 2002/0143373 A1 | 10/2002 | Courtnage et al. |
| 2002/0151888 A1 | 10/2002 | Edwards et al. |
| 2002/0183682 A1 | 12/2002 | Darvish et al. |
| 2002/0198512 A1 | 12/2002 | Seward |
| 2002/0198570 A1 | 12/2002 | Puskas |
| 2002/0198574 A1 | 12/2002 | Gumpert |
| 2003/0018344 A1 | 1/2003 | Kaji et al. |
| 2003/0023287 A1 | 1/2003 | Edwards et al. |
| 2003/0027752 A1 | 2/2003 | Steward et al. |
| 2003/0050591 A1 | 3/2003 | Patrick McHale |
| 2003/0050631 A1 | 3/2003 | Mody et al. |
| 2003/0065371 A1 | 4/2003 | Satake |
| 2003/0069570 A1 | 4/2003 | Witzel et al. |

(56) References Cited

U.S. PATENT DOCUMENTS

| | | |
|---|---|---|
| 2003/0070676 A1 | 4/2003 | Cooper et al. |
| 2003/0074039 A1 | 4/2003 | Puskas |
| 2003/0093069 A1 | 5/2003 | Panescu et al. |
| 2003/0093128 A1 | 5/2003 | Freed et al. |
| 2003/0125786 A1 | 7/2003 | Gliner et al. |
| 2003/0130657 A1 | 7/2003 | Tom et al. |
| 2003/0144572 A1 | 7/2003 | Oschman et al. |
| 2003/0153905 A1 | 8/2003 | Edwards et al. |
| 2003/0159700 A1 | 8/2003 | Laufer et al. |
| 2003/0181949 A1 | 9/2003 | Whale |
| 2003/0187430 A1 | 10/2003 | Vorisek |
| 2003/0195593 A1 | 10/2003 | Ingle et al. |
| 2003/0195604 A1 | 10/2003 | Ingle et al. |
| 2003/0202990 A1 | 10/2003 | Donovan et al. |
| 2003/0208103 A1 | 11/2003 | Sonnenschein et al. |
| 2003/0211121 A1 | 11/2003 | Donovan |
| 2003/0216791 A1 | 11/2003 | Schuler et al. |
| 2003/0216792 A1 | 11/2003 | Levin et al. |
| 2003/0216891 A1 | 11/2003 | Wegener |
| 2003/0225443 A1 | 12/2003 | Kiran et al. |
| 2003/0233099 A1 | 12/2003 | Danaek et al. |
| 2003/0236455 A1 | 12/2003 | Swanson et al. |
| 2004/0006268 A1 | 1/2004 | Gilboa et al. |
| 2004/0009180 A1 | 1/2004 | Donovan |
| 2004/0010289 A1 | 1/2004 | Biggs et al. |
| 2004/0010290 A1 | 1/2004 | Schroeppel et al. |
| 2004/0028676 A1 | 2/2004 | Klein et al. |
| 2004/0029849 A1 | 2/2004 | Schatzberg et al. |
| 2004/0030368 A1 | 2/2004 | Kemeny et al. |
| 2004/0031494 A1 | 2/2004 | Danek et al. |
| 2004/0044390 A1 | 3/2004 | Szeles |
| 2004/0059383 A1 | 3/2004 | Puskas |
| 2004/0073201 A1 | 4/2004 | Cooper et al. |
| 2004/0073206 A1 | 4/2004 | Foley et al. |
| 2004/0073278 A1 | 4/2004 | Pachys |
| 2004/0086531 A1 | 5/2004 | Barron |
| 2004/0087936 A1 | 5/2004 | Stern et al. |
| 2004/0088030 A1 | 5/2004 | Jung, Jr. |
| 2004/0088036 A1 | 5/2004 | Gilbert |
| 2004/0091880 A1 | 5/2004 | Wiebusch et al. |
| 2004/0106954 A1 | 6/2004 | Whitehurst et al. |
| 2004/0116981 A1 | 6/2004 | Mazar |
| 2004/0122488 A1 | 6/2004 | Mazar et al. |
| 2004/0122489 A1 | 6/2004 | Mazar et al. |
| 2004/0127942 A1 | 7/2004 | Yomtov et al. |
| 2004/0127958 A1 | 7/2004 | Mazar et al. |
| 2004/0142005 A1 | 7/2004 | Brooks et al. |
| 2004/0147921 A1 | 7/2004 | Edwards et al. |
| 2004/0147969 A1 | 7/2004 | Mann et al. |
| 2004/0147988 A1 | 7/2004 | Stephens |
| 2004/0151741 A1 | 8/2004 | Borodic |
| 2004/0153056 A1 | 8/2004 | Muller et al. |
| 2004/0162584 A1 | 8/2004 | Hill et al. |
| 2004/0162597 A1 | 8/2004 | Hamilton et al. |
| 2004/0167509 A1 | 8/2004 | Taimisto |
| 2004/0167580 A1 | 8/2004 | Mann et al. |
| 2004/0172075 A1 | 9/2004 | Shafer et al. |
| 2004/0172080 A1 | 9/2004 | Stadler et al. |
| 2004/0172084 A1 | 9/2004 | Knudson et al. |
| 2004/0175399 A1 | 9/2004 | Schiffman |
| 2004/0176803 A1 | 9/2004 | Whelan et al. |
| 2004/0176805 A1 | 9/2004 | Whelan et al. |
| 2004/0182399 A1 | 9/2004 | Danek et al. |
| 2004/0186435 A1 | 9/2004 | Seward |
| 2004/0204747 A1 | 10/2004 | Kemeny et al. |
| 2004/0213813 A1 | 10/2004 | Ackerman |
| 2004/0213814 A1 | 10/2004 | Ackerman |
| 2004/0215235 A1 | 10/2004 | Jackson et al. |
| 2004/0215289 A1 | 10/2004 | Fukui |
| 2004/0215296 A1 | 10/2004 | Ganz et al. |
| 2004/0220556 A1 | 11/2004 | Cooper et al. |
| 2004/0220621 A1 | 11/2004 | Zhou et al. |
| 2004/0226556 A1 | 11/2004 | Deem et al. |
| 2004/0230251 A1 | 11/2004 | Schuler et al. |
| 2004/0230252 A1 | 11/2004 | Kullok et al. |
| 2004/0243118 A1 | 12/2004 | Ayers et al. |
| 2004/0243182 A1 | 12/2004 | Cohen et al. |
| 2004/0248188 A1 | 12/2004 | Sanders |
| 2004/0249401 A1 | 12/2004 | Rabiner et al. |
| 2004/0249416 A1 | 12/2004 | Yun et al. |
| 2004/0253274 A1 | 12/2004 | Voet |
| 2005/0004609 A1 | 1/2005 | Stahmann et al. |
| 2005/0004631 A1 | 1/2005 | Benedict |
| 2005/0010263 A1 | 1/2005 | Schauerte |
| 2005/0010270 A1 | 1/2005 | Laufer |
| 2005/0015117 A1 | 1/2005 | Gerber |
| 2005/0019346 A1 | 1/2005 | Boulis |
| 2005/0021092 A1 | 1/2005 | Yun et al. |
| 2005/0049615 A1 | 3/2005 | Cooper et al. |
| 2005/0056292 A1 | 3/2005 | Cooper |
| 2005/0059153 A1 | 3/2005 | George et al. |
| 2005/0060041 A1 | 3/2005 | Phan et al. |
| 2005/0060042 A1 | 3/2005 | Phan et al. |
| 2005/0060044 A1 | 3/2005 | Roschak et al. |
| 2005/0065553 A1 | 3/2005 | Ben Ezra et al. |
| 2005/0065562 A1 | 3/2005 | Rezai |
| 2005/0065567 A1 | 3/2005 | Lee et al. |
| 2005/0065573 A1 | 3/2005 | Rezai |
| 2005/0065574 A1 | 3/2005 | Rezai |
| 2005/0065575 A1 | 3/2005 | Dobak |
| 2005/0065584 A1 | 3/2005 | Schiff et al. |
| 2005/0074461 A1 | 4/2005 | Donovan |
| 2005/0076909 A1 | 4/2005 | Stahmann et al. |
| 2005/0080461 A1 | 4/2005 | Stahmann et al. |
| 2005/0085801 A1 | 4/2005 | Cooper et al. |
| 2005/0090722 A1 | 4/2005 | Perez |
| 2005/0096529 A1 | 5/2005 | Cooper et al. |
| 2005/0096644 A1 | 5/2005 | Hall et al. |
| 2005/0107783 A1 | 5/2005 | Tom et al. |
| 2005/0107829 A1 | 5/2005 | Edwards et al. |
| 2005/0107853 A1 | 5/2005 | Krespi et al. |
| 2005/0125044 A1 | 6/2005 | Tracey |
| 2005/0137518 A1 | 6/2005 | Biggs et al. |
| 2005/0137611 A1 | 6/2005 | Escudero et al. |
| 2005/0137715 A1 | 6/2005 | Phan et al. |
| 2005/0143788 A1 | 6/2005 | Yun et al. |
| 2005/0149146 A1 | 7/2005 | Boveja et al. |
| 2005/0152924 A1 | 7/2005 | Voet |
| 2005/0153885 A1 | 7/2005 | Yun et al. |
| 2005/0159736 A9 | 7/2005 | Danek et al. |
| 2005/0165456 A1 | 7/2005 | Mann et al. |
| 2005/0171396 A1 | 8/2005 | Pankratov et al. |
| 2005/0177144 A1 | 8/2005 | Phan et al. |
| 2005/0177192 A1 | 8/2005 | Rezai et al. |
| 2005/0182288 A1 | 8/2005 | Zabara |
| 2005/0182393 A1 | 8/2005 | Abboud et al. |
| 2005/0183732 A1 | 8/2005 | Edwards |
| 2005/0187579 A1 | 8/2005 | Danek et al. |
| 2005/0193279 A1 | 9/2005 | Daners |
| 2005/0203503 A1 | 9/2005 | Edwards et al. |
| 2005/0222628 A1 | 10/2005 | Krakousky |
| 2005/0222635 A1 | 10/2005 | Krakovsky |
| 2005/0222651 A1 | 10/2005 | Jung, Jr. |
| 2005/0228054 A1 | 10/2005 | Tatton |
| 2005/0228459 A1 | 10/2005 | Levin et al. |
| 2005/0228460 A1 | 10/2005 | Levin et al. |
| 2005/0234523 A1 | 10/2005 | Levin et al. |
| 2005/0238693 A1 | 10/2005 | Whyte |
| 2005/0240176 A1 | 10/2005 | Oral et al. |
| 2005/0240241 A1 | 10/2005 | Yun et al. |
| 2005/0245992 A1 | 11/2005 | Persen et al. |
| 2005/0251128 A1 | 11/2005 | Amoah |
| 2005/0251213 A1 | 11/2005 | Freeman |
| 2005/0255317 A1 | 11/2005 | Bavaro et al. |
| 2005/0256028 A1 | 11/2005 | Yun et al. |
| 2005/0261747 A1 | 11/2005 | Schuler et al. |
| 2005/0267536 A1 | 12/2005 | Freeman et al. |
| 2005/0277993 A1 | 12/2005 | Mower |
| 2005/0283197 A1 | 12/2005 | Daum et al. |
| 2006/0015151 A1 | 1/2006 | Aldrich |
| 2006/0058692 A1 | 3/2006 | Beatty et al. |
| 2006/0058693 A1 | 3/2006 | Beatty et al. |
| 2006/0058780 A1 | 3/2006 | Edwards et al. |
| 2006/0062808 A1 | 3/2006 | Laufer et al. |

(56) References Cited

U.S. PATENT DOCUMENTS

| | | |
|---|---|---|
| 2006/0079887 A1 | 4/2006 | Buysse et al. |
| 2006/0084884 A1 | 4/2006 | Beatty et al. |
| 2006/0084966 A1 | 4/2006 | Maguire et al. |
| 2006/0084970 A1 | 4/2006 | Beatty et al. |
| 2006/0084971 A1 | 4/2006 | Beatty et al. |
| 2006/0084972 A1 | 4/2006 | Beatty et al. |
| 2006/0089637 A1 | 4/2006 | Werneth et al. |
| 2006/0095032 A1 | 5/2006 | Jackson et al. |
| 2006/0100666 A1 | 5/2006 | Wilkinson et al. |
| 2006/0106361 A1 | 5/2006 | Muni et al. |
| 2006/0111755 A1 | 5/2006 | Stone et al. |
| 2006/0116749 A1 | 6/2006 | Willink et al. |
| 2006/0135953 A1 | 6/2006 | Kania et al. |
| 2006/0135984 A1 | 6/2006 | Kramer et al. |
| 2006/0135998 A1 | 6/2006 | Libbus et al. |
| 2006/0137698 A1 | 6/2006 | Danek et al. |
| 2006/0142801 A1 | 6/2006 | Demarais et al. |
| 2006/0167498 A1 | 7/2006 | DiLorenzo |
| 2006/0178703 A1 | 8/2006 | Huston et al. |
| 2006/0206150 A1 | 9/2006 | Demarais et al. |
| 2006/0212076 A1 | 9/2006 | Demarais et al. |
| 2006/0212078 A1 | 9/2006 | Demarais et al. |
| 2006/0222667 A1 | 10/2006 | Deem et al. |
| 2006/0225742 A1 | 10/2006 | Deem et al. |
| 2006/0235474 A1 | 10/2006 | Demarais |
| 2006/0241523 A1 | 10/2006 | Sinelnikov et al. |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247683 A1 | 11/2006 | Danek et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0259028 A1 | 11/2006 | Utley et al. |
| 2006/0259029 A1 | 11/2006 | Utley et al. |
| 2006/0259030 A1 | 11/2006 | Utley et al. |
| 2006/0265014 A1 | 11/2006 | Demarais et al. |
| 2006/0265015 A1 | 11/2006 | Demarais et al. |
| 2006/0271111 A1 | 11/2006 | Demarais et al. |
| 2006/0276807 A1 | 12/2006 | Keast et al. |
| 2006/0276852 A1 | 12/2006 | Demarais et al. |
| 2006/0278243 A1 | 12/2006 | Danek et al. |
| 2006/0278244 A1 | 12/2006 | Danek et al. |
| 2006/0280772 A1 | 12/2006 | Roschak et al. |
| 2006/0280773 A1 | 12/2006 | Roschak et al. |
| 2006/0282071 A1 | 12/2006 | Utley et al. |
| 2006/0287679 A1 | 12/2006 | Stone |
| 2007/0021803 A1 | 1/2007 | Deem et al. |
| 2007/0025919 A1 | 2/2007 | Deem et al. |
| 2007/0027496 A1 | 2/2007 | Parnis et al. |
| 2007/0032788 A1 | 2/2007 | Edwards et al. |
| 2007/0043342 A1 | 2/2007 | Kleinberger |
| 2007/0055328 A1 | 3/2007 | Mayse et al. |
| 2007/0060954 A1 | 3/2007 | Cameron et al. |
| 2007/0060990 A1 | 3/2007 | Satake |
| 2007/0062545 A1 | 3/2007 | Danek et al. |
| 2007/0066957 A1 | 3/2007 | Demarais et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0083239 A1 | 4/2007 | Demarais et al. |
| 2007/0093802 A1 | 4/2007 | Danek et al. |
| 2007/0093809 A1 | 4/2007 | Edwards et al. |
| 2007/0100390 A1 | 5/2007 | Danaek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106337 A1 | 5/2007 | Errico et al. |
| 2007/0106338 A1 | 5/2007 | Errico |
| 2007/0106339 A1 | 5/2007 | Errico et al. |
| 2007/0106348 A1 | 5/2007 | Laufer |
| 2007/0112349 A1 | 5/2007 | Danek et al. |
| 2007/0118184 A1 | 5/2007 | Danek et al. |
| 2007/0118190 A1 | 5/2007 | Danek et al. |
| 2007/0123922 A1 | 5/2007 | Cooper et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2007/0129760 A1 | 6/2007 | Demarais et al. |
| 2007/0129761 A1 | 6/2007 | Demarais et al. |
| 2007/0135875 A1 | 6/2007 | Demarais et al. |
| 2007/0173899 A1 | 7/2007 | Levin et al. |
| 2007/0191902 A1 | 8/2007 | Errico et al. |
| 2007/0197896 A1 | 8/2007 | Moll et al. |
| 2007/0203549 A1 | 8/2007 | Demarais et al. |
| 2007/0225768 A1 | 9/2007 | Dobak, III |
| 2007/0232896 A1 | 10/2007 | Gilboa et al. |
| 2007/0239256 A1 | 10/2007 | Weber et al. |
| 2007/0244479 A1 | 10/2007 | Beatty et al. |
| 2007/0250050 A1 | 10/2007 | Lafontaine |
| 2007/0255270 A1 | 11/2007 | Carney |
| 2007/0255304 A1 | 11/2007 | Roschak et al. |
| 2007/0265639 A1 | 11/2007 | Danek et al. |
| 2007/0265687 A1 | 11/2007 | Deem et al. |
| 2007/0267011 A1 | 11/2007 | Deem et al. |
| 2008/0004596 A1 | 1/2008 | Yun et al. |
| 2008/0021274 A1 | 1/2008 | Bayer et al. |
| 2008/0021369 A1 | 1/2008 | Deem et al. |
| 2008/0051839 A1 | 2/2008 | Libbus et al. |
| 2008/0086107 A1 | 4/2008 | Roschak |
| 2008/0097422 A1 | 4/2008 | Edwards et al. |
| 2008/0097424 A1 | 4/2008 | Wizeman et al. |
| 2008/0125772 A1 | 5/2008 | Stone et al. |
| 2008/0147137 A1 | 6/2008 | Cohen et al. |
| 2008/0154258 A1 | 6/2008 | Chang et al. |
| 2008/0161801 A1 | 7/2008 | Steinke et al. |
| 2008/0183248 A1 | 7/2008 | Rezai et al. |
| 2008/0188912 A1 | 8/2008 | Stone et al. |
| 2008/0188913 A1 | 8/2008 | Stone et al. |
| 2008/0194956 A1 | 8/2008 | Aldrich et al. |
| 2008/0208305 A1 | 8/2008 | Rezai et al. |
| 2008/0213331 A1 | 9/2008 | Gelfand et al. |
| 2008/0234564 A1 | 9/2008 | Beatty et al. |
| 2008/0243112 A1 | 10/2008 | De Neve |
| 2008/0255449 A1 | 10/2008 | Warnking et al. |
| 2008/0255642 A1 | 10/2008 | Zarins et al. |
| 2008/0262489 A1 | 10/2008 | Steinke |
| 2008/0275445 A1 | 11/2008 | Kelly et al. |
| 2008/0302359 A1 | 12/2008 | Loomas et al. |
| 2008/0306570 A1 | 12/2008 | Rezai et al. |
| 2008/0312543 A1 | 12/2008 | Laufer et al. |
| 2008/0312725 A1 | 12/2008 | Penner |
| 2008/0319350 A1 | 12/2008 | Wallace et al. |
| 2009/0018473 A1 | 1/2009 | Aldrich et al. |
| 2009/0018538 A1 | 1/2009 | Webster et al. |
| 2009/0030477 A1 | 1/2009 | Jarrard |
| 2009/0036948 A1 | 2/2009 | Levin et al. |
| 2009/0043301 A1 | 2/2009 | Jarrard et al. |
| 2009/0043302 A1 | 2/2009 | Ford et al. |
| 2009/0048593 A1 | 2/2009 | Ganz et al. |
| 2009/0060953 A1 | 3/2009 | Sandars |
| 2009/0062873 A1 | 3/2009 | Wu et al. |
| 2009/0069797 A1 | 3/2009 | Danek et al. |
| 2009/0076409 A1 | 3/2009 | Wu et al. |
| 2009/0076491 A1 | 3/2009 | Roschak et al. |
| 2009/0112203 A1 | 4/2009 | Danek et al. |
| 2009/0124883 A1 | 5/2009 | Wibowo et al. |
| 2009/0131765 A1 | 5/2009 | Roschak et al. |
| 2009/0131928 A1 | 5/2009 | Edwards et al. |
| 2009/0131930 A1 | 5/2009 | Gelbart et al. |
| 2009/0143678 A1 | 6/2009 | Keast et al. |
| 2009/0143705 A1 | 6/2009 | Danek et al. |
| 2009/0143776 A1 | 6/2009 | Danek et al. |
| 2009/0143831 A1 | 6/2009 | Huston et al. |
| 2009/0155336 A1 | 6/2009 | Rezai |
| 2009/0177192 A1 | 7/2009 | Rioux et al. |
| 2009/0192505 A1 | 7/2009 | Askew et al. |
| 2009/0192508 A1 | 7/2009 | Laufer et al. |
| 2009/0204005 A1 | 8/2009 | Keast et al. |
| 2009/0204119 A1 | 8/2009 | Bleich et al. |
| 2009/0227885 A1 | 9/2009 | Lowery et al. |
| 2009/0227980 A1 | 9/2009 | Kangas et al. |
| 2009/0232850 A1 | 9/2009 | Manack et al. |

(56) References Cited

U.S. PATENT DOCUMENTS

| | | |
|---|---|---|
| 2009/0248011 A1 | 10/2009 | Hlavka et al. |
| 2009/0254079 A1 | 10/2009 | Edwards et al. |
| 2009/0254142 A1 | 10/2009 | Edwards et al. |
| 2009/0259274 A1 | 10/2009 | Simon et al. |
| 2009/0275840 A1 | 11/2009 | Roschak et al. |
| 2009/0275878 A1 | 11/2009 | Cambier et al. |
| 2009/0281593 A9 | 11/2009 | Errico et al. |
| 2009/0287087 A1 | 11/2009 | Gwerder et al. |
| 2009/0306644 A1 | 12/2009 | Mayse et al. |
| 2009/0318904 A9 | 12/2009 | Cooper et al. |
| 2009/0319002 A1 | 12/2009 | Simon |
| 2010/0003282 A1 | 1/2010 | Deem et al. |
| 2010/0004648 A1 | 1/2010 | Edwards et al. |
| 2010/0010564 A1 | 1/2010 | Simon |
| 2010/0016709 A1 | 1/2010 | Gilboa et al. |
| 2010/0042089 A1 | 2/2010 | Soltesz et al. |
| 2010/0049031 A1 | 2/2010 | Fruland et al. |
| 2010/0049186 A1 | 2/2010 | Ingle et al. |
| 2010/0049188 A1 | 2/2010 | Nelson et al. |
| 2010/0057178 A1 | 3/2010 | Simon |
| 2010/0063495 A1 | 3/2010 | Edwards et al. |
| 2010/0070004 A1 | 3/2010 | Hlavka et al. |
| 2010/0076518 A1 | 3/2010 | Hlavka et al. |
| 2010/0087783 A1 | 4/2010 | Weber et al. |
| 2010/0087809 A1 | 4/2010 | Edwards et al. |
| 2010/0094231 A1 | 4/2010 | Bleich et al. |
| 2010/0114087 A1 | 5/2010 | Edwards et al. |
| 2010/0116279 A9 | 5/2010 | Cooper |
| 2010/0125239 A1 | 5/2010 | Perry et al. |
| 2010/0130892 A1 | 5/2010 | Warnking |
| 2010/0137860 A1 | 6/2010 | Demarais et al. |
| 2010/0145427 A1 | 6/2010 | Gliner et al. |
| 2010/0152835 A1 | 6/2010 | Orr |
| 2010/0160906 A1 | 6/2010 | Jarrard |
| 2010/0160996 A1 | 6/2010 | Simon et al. |
| 2010/0174340 A1 | 7/2010 | Simon |
| 2010/0179424 A1 | 7/2010 | Warnking et al. |
| 2010/0185190 A1 | 7/2010 | Danek et al. |
| 2010/0191089 A1 | 7/2010 | Stebler et al. |
| 2010/0204689 A1 | 8/2010 | Danek et al. |
| 2010/0222851 A1 | 9/2010 | Deem et al. |
| 2010/0228318 A1 | 9/2010 | Errico et al. |
| 2010/0241188 A1 | 9/2010 | Errico et al. |
| 2010/0249873 A1 | 9/2010 | Errico |
| 2010/0256629 A1 | 10/2010 | Wylie et al. |
| 2010/0256630 A1 | 10/2010 | Hamilton et al. |
| 2010/0268222 A1 | 10/2010 | Danek et al. |
| 2010/0298905 A1 | 11/2010 | Simon |
| 2010/0305463 A1 | 12/2010 | Macklem et al. |
| 2010/0318020 A1 | 12/2010 | Atanasoska et al. |
| 2010/0331776 A1 | 12/2010 | Salahieh et al. |
| 2011/0004148 A1 | 1/2011 | Ishii |
| 2011/0015548 A1 | 1/2011 | Aldrich et al. |
| 2011/0028898 A1 | 2/2011 | Clark, III et al. |
| 2011/0046432 A1 | 2/2011 | Simon et al. |
| 2011/0060380 A1 | 3/2011 | Gelfand et al. |
| 2011/0079230 A1 | 4/2011 | Danek et al. |
| 2011/0093032 A1 | 4/2011 | Boggs, II et al. |
| 2011/0098762 A1 | 4/2011 | Rezai |
| 2011/0112400 A1 | 5/2011 | Emery et al. |
| 2011/0112521 A1 | 5/2011 | DeLonzor et al. |
| 2011/0118725 A1 | 5/2011 | Mayse et al. |
| 2011/0125203 A1 | 5/2011 | Simon et al. |
| 2011/0125213 A1 | 5/2011 | Simon et al. |
| 2011/0130708 A1 | 6/2011 | Perry et al. |
| 2011/0137284 A1 | 6/2011 | Arora et al. |
| 2011/0144630 A1 | 6/2011 | Loeb |
| 2011/0146673 A1 | 6/2011 | Keast et al. |
| 2011/0146674 A1 | 6/2011 | Roschak |
| 2011/0152855 A1 | 6/2011 | Mayse et al. |
| 2011/0152967 A1 | 6/2011 | Simon et al. |
| 2011/0152974 A1 | 6/2011 | Rezai et al. |
| 2011/0166499 A1 | 7/2011 | Demarais et al. |
| 2011/0166565 A1 | 7/2011 | Wizeman et al. |
| 2011/0172655 A1 | 7/2011 | Biggs et al. |
| 2011/0172658 A1 | 7/2011 | Gelbart et al. |
| 2011/0178569 A1 | 7/2011 | Parnis et al. |
| 2011/0184330 A1 | 7/2011 | Laufer et al. |
| 2011/0190569 A1 | 8/2011 | Simon et al. |
| 2011/0196288 A1 | 8/2011 | Kaplan et al. |
| 2011/0202098 A1 | 8/2011 | Demarais et al. |
| 2011/0224768 A1 | 9/2011 | Edwards |
| 2011/0230701 A1 | 9/2011 | Simon et al. |
| 2011/0230938 A1 | 9/2011 | Simon et al. |
| 2011/0245756 A1 | 10/2011 | Arora et al. |
| 2011/0251592 A1 | 10/2011 | Biggs et al. |
| 2011/0257622 A1 | 10/2011 | Salahieh et al. |
| 2011/0257647 A1 | 10/2011 | Mayse et al. |
| 2011/0263960 A1 | 10/2011 | Mitchell |
| 2011/0264086 A1 | 10/2011 | Ingle |
| 2011/0270249 A1 | 11/2011 | Utley et al. |
| 2011/0276107 A1 | 11/2011 | Simon et al. |
| 2011/0276112 A1 | 11/2011 | Simon et al. |
| 2011/0282229 A1 | 11/2011 | Danek et al. |
| 2011/0282418 A1 | 11/2011 | Saunders et al. |
| 2011/0301587 A1 | 12/2011 | Deem et al. |
| 2011/0301664 A1 | 12/2011 | Rezai |
| 2011/0301679 A1 | 12/2011 | Rezai et al. |
| 2011/0306851 A1 | 12/2011 | Wang |
| 2011/0306904 A1 | 12/2011 | Jacobson et al. |
| 2011/0306997 A9 | 12/2011 | Roschak et al. |
| 2011/0319958 A1 | 12/2011 | Simon et al. |
| 2012/0004656 A1 | 1/2012 | Jackson et al. |
| 2012/0015019 A1 | 1/2012 | Pacetti et al. |
| 2012/0016256 A1 | 1/2012 | Mabary et al. |
| 2012/0016358 A1 | 1/2012 | Mayse et al. |
| 2012/0016363 A1 | 1/2012 | Mayse et al. |
| 2012/0016364 A1 | 1/2012 | Mayse et al. |
| 2012/0029261 A1 | 2/2012 | Deem et al. |
| 2012/0029500 A1 | 2/2012 | Jenson |
| 2012/0029512 A1 | 2/2012 | Willard et al. |
| 2012/0029591 A1 | 2/2012 | Simon et al. |
| 2012/0029601 A1 | 2/2012 | Simon et al. |
| 2012/0041412 A1 | 2/2012 | Roth et al. |
| 2012/0041509 A1 | 2/2012 | Knudson et al. |
| 2012/0071870 A1 | 3/2012 | Salahieh et al. |
| 2012/0078096 A1 | 3/2012 | Krolik et al. |
| 2012/0083734 A1 | 4/2012 | Ayres et al. |
| 2012/0089078 A1 | 4/2012 | Deem et al. |
| 2012/0089138 A1 | 4/2012 | Edwards et al. |
| 2012/0101326 A1 | 4/2012 | Simon et al. |
| 2012/0101413 A1 | 4/2012 | Beetel et al. |
| 2012/0109278 A1 | 5/2012 | Sih |
| 2012/0143132 A1 | 6/2012 | Orlowski |
| 2012/0143177 A1 | 6/2012 | Avitall |
| 2012/0143179 A1 | 6/2012 | Avitall |
| 2012/0143181 A1 | 6/2012 | Demarais et al. |
| 2012/0157986 A1 | 6/2012 | Stone et al. |
| 2012/0157987 A1 | 6/2012 | Steinke et al. |
| 2012/0157988 A1 | 6/2012 | Stone et al. |
| 2012/0157989 A1 | 6/2012 | Stone et al. |
| 2012/0158101 A1 | 6/2012 | Stone et al. |
| 2012/0165803 A1 | 6/2012 | Bencini et al. |
| 2012/0184801 A1 | 7/2012 | Simon et al. |
| 2012/0185020 A1 | 7/2012 | Simon et al. |
| 2012/0191081 A1 | 7/2012 | Markowitz |
| 2012/0191082 A1 | 7/2012 | Markowitz |
| 2012/0197100 A1 | 8/2012 | Razavi et al. |
| 2012/0197246 A1 | 8/2012 | Mauch |
| 2012/0197251 A1 | 8/2012 | Edwards et al. |
| 2012/0203067 A1 | 8/2012 | Higgins et al. |
| 2012/0203216 A1 | 8/2012 | Mayse et al. |
| 2012/0203222 A1 | 8/2012 | Mayse et al. |
| 2012/0209118 A1 | 8/2012 | Warnking |
| 2012/0209259 A1 | 8/2012 | Danek et al. |
| 2012/0209261 A1 | 8/2012 | Mayse et al. |
| 2012/0209296 A1 | 8/2012 | Mayse et al. |
| 2012/0221087 A1 | 8/2012 | Parnis et al. |
| 2012/0232436 A1 | 9/2012 | Warnking |
| 2012/0245415 A1 | 9/2012 | Emura et al. |
| 2012/0253442 A1 | 10/2012 | Gliner et al. |
| 2012/0259263 A1 | 10/2012 | Celermajer et al. |
| 2012/0259269 A1 | 10/2012 | Meyer |
| 2012/0259326 A1 | 10/2012 | Brannan et al. |

(56) References Cited

U.S. PATENT DOCUMENTS

| | | |
|---|---|---|
| 2012/0265280 A1 | 10/2012 | Errico et al. |
| 2012/0289952 A1 | 11/2012 | Utley et al. |
| 2012/0290035 A1 | 11/2012 | Levine et al. |
| 2012/0294424 A1 | 11/2012 | Chin et al. |
| 2012/0296329 A1 | 11/2012 | Ng |
| 2012/0310233 A1 | 12/2012 | Dimmer et al. |
| 2012/0316552 A1 | 12/2012 | Mayse et al. |
| 2012/0316559 A1 | 12/2012 | Mayse et al. |
| 2012/0330298 A1 | 12/2012 | Ganz et al. |
| 2013/0012844 A1 | 1/2013 | Demarais et al. |
| 2013/0012866 A1 | 1/2013 | Deem et al. |
| 2013/0012867 A1 | 1/2013 | Demarais et al. |
| 2013/0035576 A1 | 2/2013 | O'Grady et al. |

FOREIGN PATENT DOCUMENTS

| | | |
|---|---|---|
| CN | 101115448 B | 5/2010 |
| DE | 19529634 A1 | 2/1997 |
| DE | 19952505 | 5/2001 |
| EP | 189329 A3 | 6/1987 |
| EP | 286145 A2 | 10/1988 |
| EP | 280225 A3 | 3/1989 |
| EP | 282225 B1 | 6/1992 |
| EP | 0 643 982 | 3/1995 |
| EP | 908713 A1 | 4/1999 |
| EP | 1 143 864 | 10/2001 |
| EP | 1 271 384 | 1/2003 |
| EP | 1 281 366 | 2/2003 |
| EP | 908150 B1 | 5/2003 |
| EP | 1 326 549 | 7/2003 |
| EP | 768091 B1 | 7/2003 |
| EP | 1326548 | 7/2003 |
| EP | 1 400 204 | 3/2004 |
| EP | 1297795 B1 | 8/2005 |
| EP | 1 588 662 | 10/2005 |
| FR | 2659240 B1 | 7/1997 |
| GB | 2233293 A | 1/1991 |
| GB | 2233293 | 2/1994 |
| JP | 59167707 A2 | 9/1984 |
| JP | 7289557 A2 | 11/1995 |
| JP | 9047518 A2 | 2/1997 |
| JP | 9243837 A2 | 9/1997 |
| JP | 10026709 A2 | 1/1998 |
| RU | 2053814 | 2/1996 |
| RU | 2091054 C1 | 9/1997 |
| SU | 545358 T | 2/1977 |
| WO | 89/11311 | 11/1989 |
| WO | 93/01862 | 2/1993 |
| WO | 93/16632 | 9/1993 |
| WO | 94/07446 | 4/1994 |
| WO | 95/01075 | 1/1995 |
| WO | WO-9502370 | 1/1995 |
| WO | WO-9510322 A1 | 4/1995 |
| WO | WO-9604860 A1 | 2/1996 |
| WO | WO-9610961 A1 | 4/1996 |
| WO | 97/25917 | 7/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | 98/18391 | 5/1998 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO-9903413 A1 | 1/1999 |
| WO | WO-9858681 A3 | 3/1999 |
| WO | WO-9913779 A2 | 3/1999 |
| WO | WO-9932040 A1 | 7/1999 |
| WO | 99/42047 | 8/1999 |
| WO | WO-9964109 A1 | 12/1999 |
| WO | 00/10598 | 3/2000 |
| WO | WO-0051510 A1 | 9/2000 |
| WO | 00/62699 | 10/2000 |
| WO | 00/66017 | 11/2000 |
| WO | 01/00114 | 1/2001 |
| WO | WO-0103642 A1 | 1/2001 |
| WO | 01/70114 | 9/2001 |
| WO | 01/89526 | 11/2001 |
| WO | WO-0205720 | 1/2002 |
| WO | WO-0205868 | 1/2002 |
| WO | WO-0232333 A1 | 4/2002 |
| WO | WO-0232334 A1 | 4/2002 |
| WO | 03/073358 | 9/2003 |
| WO | 03/088820 | 10/2003 |
| WO | 2004/078252 | 9/2004 |
| WO | 2004/082736 | 9/2004 |
| WO | 2004/101028 | 11/2004 |
| WO | 2005/006963 | 1/2005 |
| WO | 2005/006964 | 1/2005 |
| WO | 2006/053308 | 5/2006 |
| WO | 2006/053309 | 5/2006 |
| WO | 2006/116198 | 11/2006 |
| WO | 2007/058780 A9 | 5/2007 |
| WO | 2007/061982 | 5/2007 |
| WO | 2007/092062 A1 | 8/2007 |
| WO | 2007/094828 A3 | 8/2007 |
| WO | 2007/143665 | 12/2007 |
| WO | 2008/005953 | 1/2008 |
| WO | 2008/024220 | 2/2008 |
| WO | 2008/051706 | 5/2008 |
| WO | 2008/063935 | 5/2008 |
| WO | 2009/009236 | 1/2009 |
| WO | 2009/015278 | 1/2009 |
| WO | WO-2009082433 A2 | 7/2009 |
| WO | 2009/126383 A3 | 10/2009 |
| WO | WO-2009137819 A1 | 11/2009 |
| WO | 2010/110785 A1 | 9/2010 |
| WO | WO-2011060200 | 5/2011 |

OTHER PUBLICATIONS

Awadh, N., et al. "Airway Wall Thickness in Patients With Near Fatal Asthma and Control Groups: Assessment With High Resolution Computed Tomographic Scanning," *Thorax* 53:248-253, 1998.

Babichev et al., "Clinico-morphological comparisons in patients with bronchial asthma after denervation of the lungs," *Soy Med.* 12:13-16, 1985.

Babichev et al., "Long-term results of surgical treatment of bronchial asthma based on adaptive response," *Khirurgiia (Mosk)* 4:5-11, 1993.

Babichev et al., "Partial deneration of the lungs in bronchial asthma," *Khirurgiia (Mosk)* 4:31-35, 1985.

Barlaw, "Surgical Treatment of Asthma," *Postgrad Med. Journal* 25:193-196, 1949.

Bel, E, H., Hot Stuff: Bronchial Thermoplasty for Asthma, American Journal of Respiratory and Critical Care Medicine, 2006, vol. 173, pp. 941-942.

Bertog, S., "Covidien-Maya: OneShot™," presentation at the 2012 Congenital & Structural Interventions Congress in Frankfurt, Germany, Jun. 28, 2012, 25 pages.

Bester et al., "Recovery of C-Fiber-Induced Extravasation Following Peripheral Nerve Injury in the Rat," *Experimental Neurology* 154:628-636, 1998.

Bigalke et al., "Clostridial Neurotoxins," *Handbook of Experimental Pharmacology* (Aktories, K., and Just, I., eds) 145:407-443, 2000.

Bittner et al., "Isolated Light Chains of Botulinum Neurotoxins Inhibit Exocytosis," *The Journal of Biological Chemistry* 264(18):10354-10360, 1989.

Blindt et al., "Development of a New Biodegradable Intravascular Polymer Stent with Simultaneous Incorporation of Bioactive Substances," *The International Journal of Artificial Organs* 22(12):843-853, 1999.

Bradley et al., "Effect of vagotomy on the breathing pattern and exercise ability in emphysematous patients," *Clinical Science* 62:311-319, 1982.

Breekveldt-Postma et al., "Enhanced persistence with tiotropium compared with other respiratory drugs in COPD," *Respiratory Medicine* 101:1398-1405, 2007.

Brody et al., "Mucociliary clearance after lung denervation and bronchial transection," *J. Applied Physiology* 32(2):160-164, 1972.

(56) References Cited

OTHER PUBLICATIONS

Brown, R. H. et al., Effect of bronchial thermoplasty on airway distensibility, European Respiratory Journal, vol. 26, No. 2, pp. 277-282.
Brown, R. H. et al., In vivo evaluation of the effectiveness of bronchial thermoplasty with computed tomography. Journal of Applied Physiology, 2005, vol. 98, pp. 1603-1606.
Buzzi, "Diphtheria Toxin Treatment of Human Advanced Cancer," *Cancer Research* 42:2054-2058, 1982.
Canning et al., "Reflex Mechanisms in Gastroesophageal Reflux Disease and Asthma," *The American Journal of Medicine* 115(3A):45S-48S, 2003.
Canning et al., "Reflex Mechanisms in Gastroesophageal Reflux Disease and Asthma," *Am J Med.* 115(Suppl 3A):45S-48S, 2003. (Abstract only.).
Canning, "Reflex regulation of airway smooth muscle tone," *J Appl. Physiol.* (101):971-985, 2006.
Castro, M., et al., "Effectiveness and Safety of Bronchial Thermoplasty in the Treatment of Severe Asthma: A Multicenter, Randomized, Double-Blind, Sham-Controlled Clinical Trial," *American Journal of Respiratory and Critical Care Medicine 181*: 116-124, 2010.
Chaddock et al. "Expression and Purification of Catalytically Active, Non-Toxic Endopeptidase Derivatives of *Clostridium Botulinum* Toxin Type A," *Protein Expression and Purification* 25(2):219-228, Jul. 2002.
Chang, "Cell poration and cell fusion using an oscillating electric field," *Biophys. J. 56*:641-652, 1989.
Chernyshova et al., "The Effect of Low-Energy Laser Radiation in the Infrared Spectrum on Bronchial Patency in Children With Bronchial Asthma," *Vopr Kurortol, Fizioter Lech Fiz Kult 2*:11-14, 1995.
Chhajed, P., Will There be a Role for Bronchoscopic Radiofrequency Ablation?, 2005, J Bronchol, vol. 12, No. 3, p. 184.
Chumakov et al., "Morphologic Studies of Bronchial Biopsies in Chronic Bronchitis Before and After Treatment," *Arkh. Patol. 57*(6):21-25, 1995. (+ English abstract and translation, 8 pages.).
Co-Pending U.S. Appl. No. 12/372,607, filed Feb. 17, 2009, Edwin J. Hlavka et al.
Co-Pending U.S. Appl. No. 13/523,223, filed Jun. 14, 2012, Edwin J. Hlavka et al.
Co-pending U.S. Appl. No. 09/095,323.
Co-pending U.S. Appl. No. 09/244,173.
Cox, G. et al., Asthma Control During the Year After Bronchial Thermoplasty, The New England Journal of Medicine, Mar. 29, 2007, vol. 356, No. 13, pp. 1327-1337.
Cox, G., et al, . Early Clinical Experience With Bronchial Thermoplasty for the Treatment of Asthma, 2002, p. 1068.
Cox, G., et al., Bronchial Thermoplasty for Asthma, American Journal of Respiratory and Critical Care Medicine, 2006, vol. 173, pp. 965-969.
Cox, G., et al., Bronchial Thermoplasty: Long-Term Follow-up and Patient Satisfaction, 2004, p. 1.
Abbott, "Present Concepts Relative to Autonomic Nerve Surgery in the Treatment of Pulmonary Disease," *American Journal of Surgery 90*:479-489, 1955.
Accad, M., "Single-Step Renal Denervation With the OneShot™ Ablation System," presentation at the Leipzig Interventional Course 2012 in Leipzig, Germany, Jan. 26, 2012, 11 pages.
Ahnert-Hilger et al., "Introduction of Macromolecules into Bovine Adrenal-Medullary Chromaffin Cells and Rat Pheochromocytoma Cells (PC12) by Permeabilization with Streptolysin O: Inhibitory Effect of Tetanus Toxin on Catecholamine Secretion," *J. Neurochem 52*(6):1751-1758, Jun. 1989.
Amendment After Allowance filed Sep. 17, 2012, in co-pending U.S. Appl. No. 12/372,607, filed Feb. 17, 2009, Edwin J. Hlavka et al.
Cox, G., et al., Clinical Experience with Bronchial Thermoplasty for the Treatment of Asthma, 2003, Chest 124, p. 106S.
Cox, G., et al., Development of a Novel Bronchoscope Therapy for Asthma, Journal of Allergy and Clinical Immunology, 2003, p. 1.
Cox, G., et al., Impact of bronchial thermoplasty on asthma status: interim results from the AIR trial, 2006, European Respiratory Society Annual. Meeting, Munich, Germany, p. 1.
Cox, G., et al., Radiofrequency ablation of airway smooth muscle for sustained treatment of asthma: preliminary investigations, European Respiratory Journal, 2004, 24, pp. 659-663.
Cox. G. et al., Bronchial Thermoplasty: One-Year Update, American Thoracic Society Annual Meeting, 2004, p. 1.
Crimi et al., "Protective effects of inhaled ipratropium bromide on bronchoconstriction induced by adenosine and methacholine in asthma," *Eur Respir J 5*:560-565, 1992.
Danek, C. J., et al., Asthma Intervention Research (AIR) Trial Evaluating Bronchial Thermoplasty™; Early Results, 2002, American Thoracic Society Annual Meeting, p. 1.
Danek, C. J., et al., Bronchial thermoplasty reduces canine airway responsiveness to local methacholine challenge, 2002, American Thoracic Society Annual Meeting, p. 1.
Danek, C. J., et al., Reduction in airway hyperesponsiveness to methacholine by the application of RF energy in dogs, J Appl Physiol, 2004, vol. 97, pp. 1946-1933.
De Paiva et al., "Light chain of botulinum neurotoxin is active in mammalian motor nerve terminals when delivered via liposomes," *FEBS Lett. 17*:277(1-2): 171-174, Dec. 1990.
Dierkesmann et al., Indication and Results of Endobronchial Laser Therapy, Lung, 1990, 168, 1095-1102.
Dimitrov-Szokodi et al., "Lung Denervation in the Therapy of Intractable Bronchial Asthma," *J. Thoracic Surg. 33*(2):166-184, Feb. 1957.
Donohue et al., "A 6-Month, Placebo-Controlled Study Comparing Lung Function and Health Status Changes in COPD Patients Treated With Tiotropium or Salmeterol," *Chest* 122:47-55, 2002.
Evis Exera Bronchovideoscope Brochure, Olympus BF-XT160, Olympus, Jun. 15, 2007, 2 pages.
Feshenko et al., "Clinico-morphological comparisons in the laser therapy of chronic bronchitis patients," *Lik Sprava.* (10-12):75-79, 1993. (+ English abstract, 1 Page).
Friedman et al., "Healthcare Costs with Tiotropium Plus Usual Care versus Usual Care Alone Following 1 Year of Treatment in Patients with Chronic Obstructive Pulmonary Disorder (COPD)," *Pharmacoeconomics 22*(11):741-749, 2004.
Gaude, G.S., "Pulmonary Manifestations of Gastroesophageal Reflux Disease," *Annals of Thoracic Medicine 4*(3):115-123, Jul.-Sep. 2009.
Gelb et al., "Laser in treatment of lung cancer," *Chest 86*(5):662-666, 1984.
George et al., "Factors Associated With Medication Nonadherence in Patients With COPD," *Chest* 128:3198-3204, 2005.
Gerasin et al., "Endobronchial electrosurgery," *Chest 93*:270-274, 1988.
Gibson et al., "Gastroesophageal Reflux Treatment for Asthma in Adults and Children," *Cochrane Database Syst. Rev. 2*:CD001496, 2003. (Abstract only.).
Glanville et al., "Bronchial responsiveness after human heart-lung transplantation," *Chest 97*(6):1360-1366, 1990.
Glanville et al., "Bronchial responsiveness to exercise after human cardiopulmonary transplantation," *Chest 96*(2):81-286, 1989.
Global Strategy for Asthma Management and Prevention, 2002, 192 Pages Total.
Gosens et al., "Muscarinic receptor signaling in the pathophysiology of asthma and COPD," *Respiratory Research 7*(73):1-15, 2006.
Groeben et al. "High Thoracic Epidural Anesthesia Does Not Alter Airway Resistance and Attenuates the Response to an Inhalational Provocation Test in Patients with Bronchial Hyperreactivity," *Anesthesiology 81*(4):868-874, 1994.
Guarini et al., "Efferent Vagal Fibre Stimulation Blunts Nuclear Factor-kB Activation and Protects Against Hypovolemic Hemmorrhagic Shock," *Circulation 107*:1189-1194, 2003.
Guzmán et al., "Bioeffects Caused by Changes in Acoustic Cavitation Bubble Density and Cell Concentration: A Unified Explanation Based on Cell-to-Bubble Ratio and Blast Radius," *Ultrasound in Med. & Biol. 29*(8):1211-1222, 2003.
Hainsworth et al., "Afferent lung denervation by brief inhalation of steam," *Journal of Applied Physiology* (34)5: 708-714, 1972.

(56) References Cited

OTHER PUBLICATIONS

Harding, "Recent Clinical Investigations Examining the Association of Asthma and Gastroesophageal Reflux," *Am J Med.* 115(Suppl 3A):39S-44S, 2003. (Abstract only.).
Hiraga, "Experimental surgical therapy of bronchial asthma. The effect of denervation in dogs," *Nihon Kyobu Shikkan Gakkai Zasshi* 19(1):46-56, 1981.
Hoffmann et al., "Inhibition of Histamine-Induced Bronchoconstriction in Guinea Pig and Swine by Pulsed Electrical Vagus Nerve Stimulation," *Neuromodulation: Technology at the Neural Interface*:1-9, 2009.
Hooper et al., "Endobronchial electrocautery," *Chest* 87(6):12-714, 1985.
Ivanyuta OM, et al., "Effect of Low-Power Laser Irradiation of Bronchia Mucosa on the State of Systemic and Local Immunity in Patients with Chronic Bronchitis," *Problemy Tuberkuleza* 6:26-29, 1991.
James C. Hogg, The Pathology of Asthma, APMIS, Oct. 1997, 105(10), 735-745.
James, et al., "The Mechanics of Airway Narrowing in Asthma," Am. Rev. Respir. Dis., 1989, 139, 242-246.
Jammes et al., "Assessment of the Pulmonary Origin of Bronchoconstrictor Vagal Tone," *J. Physiol.* 291: 305-316, 1979.
Janssen L. J., "Asthma therapy: how far have we come, why did we fail and where should we go next?," Eur Respir J, 2009, 33, pp. 11-20.
Jiang et al., "Effects of Antireflux Treatment on Bronchial Hyperresponsiveness and Lung Function in Asthmatic Patients with Gastroesophageal Reflux Disease," *World J Gastroenterol.* 9:1123-1125, 2003. (Abstract only.).
Karashurov et al., "Electrostimulation in the therapy of bronchial asthma," *Klin Med (Mosk)* 79(11):38-41, 2001.
Karashurov et al., "Radiofrequency electrostimulation of carotid sinus nerves for the treatment of bronchial asthma," *Khirurgiia (Mosk)* 12:2-6, 1999.
Khmel'kova et al., "Does laser irridation affect bronchial obstruction?," *Probl Tuberk* 3:41-42, 1995. (Abstract only.).
Khoshoo et al., "Role of Gastroesophageal Reflux in Older Children with Persistent Asthma," *Chest* 123:1008-1013, 2003. (Abstract only.).
Kiljander, "The Role of Proton Pump Inhibitors in the Management of Gastroesophageal Reflux Disease-Related Asthma and Chronic Cough," *Am J Med.* 115(Suppl 3A):65S-71S, 2003. (Abstract only.).
Kistner et al., "Reductive Cleavage of Tetanus Toxin and Botulinum Neurotoxin A by the Thioredoxin System from Brain," *Naunyn-Schmiedebergs Arch Pharmacol* 345(2):227-234, Feb. 1992.
Kitamura S., "Color Atlas of Clinical Application of Fiberoptic Bronchoscopy," 1990, Year Book Medical Publishers, 17.
Kletskin et al., "Value of assessing the autonomic nervous system in bronchial asthma in selecting the surgical treatment method," *Khirurgiia (Mosk)* 7:91-95, 1987.
Kliachkin et al., "Bronchoscopy in the treatment of bronchial asthma of infectious allergic origin," *Ter Arkh* 54(4):76-79, 1982.
Korochkin et al., "Use of a Helium-Neon Laser in Combined Treatment of Bronchial Asthma," *New Developments in Diagnostics and Treatment*, 1990, 9 pgs.
Korpela et al., "Comparison of Tissue Reactions in the Tracheal Mucosa Surrounding a Bioabsorbable and Silicone Airway Stents," *Annals of Thoracic Surgery* 66:1772-1776, 1998.
Kozaki et al., "New surgical treatment of bronchial asthma— denervation of the hilus pulmonis (2)," *Nippon Kyobu Geka Gakkai Zasshi* 22(5):465-466, 1974.
Kraft M., "The distal airways: are they Important in asthma?," European Respiratory, 1999, 1403-1417.
Kreitman, "Taming ricin toxin," *Nature Biotechnology* 21:372-374, 2003.
Kuntz, "The Autonomic Nervous System in Relation to the Thoracic Viscera," *Chest* 10:1-18, 1944.
Laufer, "Method and Apparatus for Treating Smooth Muscles in the Walls of Body Conduits," U.S. Appl. No. 09/095,323, filed Jun. 10, 1998, 25 pages.

Lavioletts, et al. Asthma Intervention Research (AIR) Trial: Early Safety Assessment of Bronchial Thermoplasty, 2004, p. 1.
Leff et al., Bronchial Thermoplasty Alters Airway Smooth Muscle and Reduces Responsiveness in Dogs; A Possible Procedure for the Treatment of Asthma, American Thoracic Society Annual Meeting, 2002, p. 1.
Lennerz et al., "Electrophysiological characterization of vagal afferents relevant to mucosal nociception in the rat upper oesophagus," *J. Physiol.* 582(1):229-242, 2007.
Levin, "The Treatment of Bronchial Asthma by Dorsal Sympathectomy," *Annals of Surgery* 102(2):161-170, 1935.
Lim, E.E. et al., Botulinum Toxin: A Novel Therapeutic Option for Bronchial Asthma?, Medical Hypotheses, 2006, vol. 66, pp. 915-919.
Liou et al., "Causative and Contributive Factors to Asthmas Severity and Patterns of Medication Use in Patients Seeking Specialized Asthma Care," *Chest* 124:1781-1788, 2003. (Abstract only.).
Løkke et al., "Developing COPD: a 25 year follow up study of the general population," *Thorax* 61:935-939, 2006.
Lombard, et al, Histologic Effects of Bronchial Thermoplasty of Canine and Human Airways, American Thoracic Society Annual Meeting, 2002, p. 1.
Macklem P.T., Mechanical Factors Determining Maximum Bronchoconstriction, European Respiratory Journal, Jun. 1989, 6, 516s-519s.
Maesen et al., "Tiotropium bromide, a new long-acting antimuscarinic bronchodilator: a pharmacodynamic study in patients with chronic obstructive pulmonary disease (COPD)," *Eur. Respi. J.* 8:1506-1513, 1995.
Magnussen et al., "Effect of Inhaled Ipratropium Bromide on the Airway Response to Methacholine, Histamine, and Exercise in Patients with Mild Bronchial Asthma," *Respiration* 59:42-47, 1992.
Maltais et al., "Improvements in Symptom-Limited Exercise Performance Over 8 h With Once-Daily Tiotropium in Patients With COPD," *Chest* 128:1168-1178, 2005.
Martin, N., et al., "Bronchial Thermoplasty for the Treatment of Asthma," *Current Allergy and Asthma Reports* 9(1):88-95, Jan. 2009.
Mathew et al., "Gastro-oesophageal reflux and bronchial asthma: current status and future directions," *Postgrad Med. J.* 80:701-705, 2004.
Mayse, M. et al., Clinical Pearls for Bronchial Thermoplasty, J Bronchol, Apr. 2007, vol. 14, No. 2, pp. 115-123.
McEvoy, C.E., et al., "Changing the Landscape: Bronchial Thermoplasty Offers a Novel Approach to Asthma Treatment," *Advance for Managers of Respiratory Care*, pp. 22, Oct. 24-25, 2007.
McKay et al., "Autocrine regulation of asthmatic airway inflammation: role of airway smooth muscle," *Respir Res* 3(11):1-13, 2002.
Mehta et al., "Effect of endobronchial radiation therapy on malignant bronchial obstruction," *Chest* 97(3):662-665, 1990.
Meshalkin et al., "Partial denervation of the pulmonary hilus as one of the methods of surgical treatment of bronchial asthma," *Grudn Khir* 1:109-111, 1975.
Michaud, G., et al., "Positioned for Success: Interest in Diagnostic and Therapeutic Bronchoscopy is Growing," *Advance for Managers of Respiratory Care*, pp. 40, 42-43, Jul./Aug. 2008.
Miller, J. D. et al., Bronchial Thermoplasty is Well Tolerated by Non-Asthmatic Patients Requiring Lobectomy, 2002, American Thoracic Society Annual Meeting, p. 1.
Miller. J. D. et al., A Prospective Feasibility Study of Bronchial Thermoplasty in the Human Airway. 2005. vol. 127, No. 6 pp. 1999-2006.
Montaudon, M., et al., "Assessment of bronchial wall thickness and lumen diameter in human adults using multi-detector computed tomography: comparison with theoretical models," *J. Anat.* 211:579-588, 2007.
Moore, Keith L., *Clinically Oriented Anatomy*, $2^{nd}$ ed., Williams & Wilkins, Baltimore, 1985, pp. 85 and 87. (Abstract only.).
Netter F.H., Respiratory System: A Compilation of Paintings Depicting Anatomy and Embryology, Physiology, Pathology, Pathophysiology, and Clinical Features and Treatment of Diseases, in The Ciba Collection of Medical Illustrations M.B. Divertie, ed., Summit New Jersey, 1979, vol. 7, 119-135.

(56) References Cited

OTHER PUBLICATIONS

Netter, Frank H., *The Ciba Collection of Medical Illustrations*: vol. 7, Respiratory System, Ciba-Geigy Corporation, West Caldwell, 1979, p. 23, section 1. (Abstract only.).
Non-Final Office Action for U.S. Appl. No. 11/398,353; Mailed on Aug. 31, 2009; 7 pages.
Non-Final Office Action for U.S. Appl. No. 11/398,353; Mailed on Apr. 27, 2010; 8 pages.
Notice of final Rejection, Japanese Patent Application No. 2000-553172, dated Sep. 2, 2008, 5 pages.
O'Connor et al., "Prolonged Effect of Tiotropium Bromide on Methacholine-induced Bronchoconstriction in Asthma," *Am. J. Respir. Crit. Care Med. 154*:876-880, 1996.
O'Sullivan, M.P., et al., "Apoptosis in the Airways: Another Balancing Act in the Epithelial Program," *American Journal of Respiratory Cell and Molecular Biology 29*:3-7, 2003.
Ochs, Matthias et al., Fisherman, Alfred P., et al. (eds), *Functional Design of the Human Lung for Gas Exchange*, 4th ed., McGraw Hill Medical, New York, 2008, Chap. 2, "Fisherman's Pulmonary Diseases and Disorders." (Abstract only.).
Ovcharenko et al., "Endobronchial use of low-frequency ultrasound and ultraviolet laser radiation in the complex treatment of patients with suppurative bronchial diseases," *Probl Tuberk 3*:40-42, 1997. (Abstract only.).
Overholt, "Glomectomy for Asthma," *Dis Chest 40*:605-610, 1961.
Pavord, I.D., et al., "Safety and Efficacy of Bronchial Thermoplasty in Symptomatic, Severe Asthma," *American Journal of Respiratory and Critical Care Medicine 176*:1185-1191, 2007.
PCT International search report for application No. PCT/US00/05412 mailed on Jun. 20, 2000, 2 pages.
PCT International search report for application No. PCT/US00/18197 mailed on Oct. 3, 2000, 1 page.
PCT International search report for application No. PCT/US00/28745 mailed on Mar. 28, 2001, 6 pages.
PCT International search report for application No. PCT/US01/32321 mailed on Jan. 18, 2002, 2 pages.
PCT International search report for application No. PCT/US98/03759 mailed on Jul. 30, 1998, 1 page.
PCT International search report for application No. PCT/US98/26227 mailed on Mar. 25, 1999, 1 page.
PCT International search report for application No. PCT/US99/00232 mailed on Mar. 4, 1999, 1 page.
PCT International search report for application No. PCT/US99/12986 mailed on Sep. 29, 1999, 1 page.
Peter K. Jeffery, "Remodeling in Asthma and Chronic Obstructive Lung Disease," American Journal of Respiratory and Critical Care Medicine, 2001, 164 (10), 13516.
Peters et al., "Tiotropium Bromide Step-Up Therapy for Adults with Uncontrolled Asthma," *New England Journal of Medicine 363*(18):1715-1726, Oct. 28, 2010.
Petrou, et al., "Bronchoscopic Diathermy Resection and Stent Insertion: a Cost Effective Treatment for Tracheobronchial Obstruction," *Thorax 48*:1156-1159, 1993.
Polosukhin, "Dynamics of the ultrastructural changes in blood and lymphatic capillaries of bronchi in inflammation and following endobronchial laser therapy," *Virchows Arch. 431*:283-290, 1997.
Polosukhin, "Regeneration of Bronchial Epithelium on Chronic Inflammatory Changes Under Laser Treatment," *Path. Res. Pract. 192*:909-918, 1996.
Polosukhin, "Ultrastructural study of the destructive and repair processes in pulmonary inflammation and following endobronchial laser therapy," *Virchows Arch. 435*:13-19, 1999.
Polosukhin, "Ultrastructure of the Blood and Lymphatic Capillaries of the Respiratory Tissue During Inflammation and Endobronchial Laser Therapy," *Ultrastructural Pathology 24*:183-189, 2000.
Preliminary Amendment and Response to Restriction Requirement filed Oct. 22, 2013, in co-pending U.S. Appl. No. 13/523,223, filed Jun. 14, 2012, Edwin J. Hlavka et al.
Provotorov et al.; The Clinical Efficacy of Treating Patients with Nonspecific Lung Disease by Using Low-energy Laser Irradiation and Intrapulmonary Drug Administration, ISSN: 0040-3660., Terapevticheskii Arkhiv (USSR), 1991, 63 (12), 18-23.
Provotorov VM, et al., "Clinical Efficacy of Treatment of Patients with Non-Specific Pulmonary Diseases by Using Low-Power Laser Irradiation and Performing Intrapulmonary Drug Administration," *Terapevichesky Arkhiv 62*:18-23, 1991.
Raj, "Editorial," *Pain Practice 4*(1S):S1-53, 2004.
Ramirez et al., "Sympathetomy in Bronchial Asthma," *J. A. M. A. 84* (26):2002-2003, 1925.
Rienhoff et al., "Treatment of Intractable Bronchial Asthma by Bilateral Resection of the Posterior Pulmonary Plexus," *Arch Surg 37*(3):456-469, 1938.
Rocha-Singh, K.J., "Renal Artery Denervation: A Brave New Frontier," *Endovascular Today*, Feb. 2012, pp. 45-53.
Rubin, et al., Bronchial Thermoplasty improves Asthma Status of Moderate to Severe Persistent Asthmatics Over and Above Current Standard-of-Care, 2006, American College of Chest Physicians, 2 pages.
Savchenko et al., "Adaptation of regulatory physiological systems in surgical treatment of patients with bronchial asthma," *Klin Med (Mosk) 74*(7):38-39, 1996.
Sengupta, "Part 1 Oral cavity, pharynx and esophagus—Esophageal sensory physiology," *GI Motility online*:17 pages, 2006.
Seow C. Y., et al al. "Signal Transduction in Smooth Muscle Historical perspective on airway smooth muscle: the saga of a frustrated cell," J Appl Physiol, 2001, 91, 938-952.
Sepulveda et al., "Treatment of Asthmatic Bronchoconstriction by Percutaneous Low Voltage Vagal Nerve Stimulation: Case Report," *Internet Journal of Asthma, Allergy, and Immunology 7*(2):3 pages, 2009.
Shaari et al., "Rhinorrhea is Decreased in Dogs After Nasal Application of Botulinum Toxin," *Otolaryngol Head Neck Surg 112*(14):566-571, 1992.
Sheski FD, et al., "Cryotherapy, Electrocautery, and Brachytherapy," *Clinics in Chest Medicine 20*(1):123-138, Mar. 1999.
Shesterina. M. V. et al., Effect of laser therapy on immunity in patients with bronchial asthma and pulmonary tuberculosis, 1993, pp. 23-26.
Sil'vestrov et al., "The Clinico-Pathogenetic Validation and Efficacy of the Use of Low-Energy Laser Irradiation and Glucocorticoids in the Treatment of Bronchial Asthma Patients," *Ter Arkh 63*(11), 87-92, 1991.
Simon R. Johnson et al., Synthetic Functions of Airway Smooth Muscle in Asthma, Trends Pharmacol. Sci., Aug. 1997, 18(8), 288-292.
Simonsson et al., "Role of Autonomic Nervous System and the Cough Reflex in the Increased Responsiveness of Airways in Patients with Obstructive Airway Disease," *The Journal of Clinical Investigation 46*(11): 1812-1818, 1967.
Simpson et al., "Isolation and Characterization of the *Botulinum* Neurotoxins," *Methods Enzymol 165*:76-85, 1988.
Smakov, "Denervation of the lung in the treatment of bronchial asthma," *Khirurgiia (Mosk)* 9:117-120, 1982.
Smakov, "Pathogenetic substantiation of lung denervation in bronchial asthma and it's indications," *Khirurgiia (Mosk)* 2:67-69, 1999.
Smakov, "Prognostication of the effect of therapeutic bronchoscopy in patients with bronchial asthma according to the state of local immunity," *Klin Med (Mosk) 73*(5):76-77, 1995.
Solway, J. et al., Airway Smooth Muscle as a Target for Asthma Therapy, The New England Journal of Medicine, Mar. 29, 2007, 356(13), pp. 1367-1369.
Sontag et al., "Asthmatics with Gastroesophageal Reflux: Long-term Results of a Randomized Trial of Medical and Surgical Antireflux Therapies," *Am J Gastroenterol. 98*:987-999, 2003. (Abstract only.).
Stein, "Possible Mechanisms of Influence of Esophageal Acid on Airway Hyperresponsiveness," *Am J Med. 115*(Suppl 3A):55S-59S, 2003. (Abstract only.).
Stephanie A.Shore, "Airway Smooth Muscle in Asthma—Not Just More of the Same." N Engl J Med, 2004, 351 (6), 531-532.
Sterk, P. J., Heterogeneity of Airway Hyperresponsiveness: Time for Unconventional, but Traditional Studies, 2004, The American Pshychoiogical Society, pp. 2017-2018.

(56) References Cited

OTHER PUBLICATIONS

Sundaram et al., "An Experimental and Theoretical Analysis of Ultrasound-Induced Permeabilization of Cell Membranes," *Biophysical Journal 84*:3087-3101, 2003.
Takino et al., "Surgical Removal of the Carotid Body and its Relation to the Carotid Chemoreceptor and Baroreceptor Reflex in Asthmatics," *Dis Chest 47*:129-138, 1965.
Tashkin et al., "Long-term Treatment Benefits With Tiotropium in COPD Patients With and Without Short-term Bronchodilator Responses," *Chest* 123: 1441-1449, 2003.
Toma, T. P., Brave New World for Interventional Bronchoscopy, 2005, Thorax, vol. 60, pp. 180-181.
Trow, T., Clinical Year in Review I, proceedings of the American Thoracic Society, 2006, vol. 3, pp. 553-556.
Tschumperlin, D.J., et al., "Chronic Effects of Mechanical Force on Airways," *Annual Review of Physiology 68*: 563-83, 2006.
Tschumperlin, D.J., et al., "Mechanical Stimuli to Airway Remodeling," *American Journal of Respiratory and Critical Care Medicine 164*:S90-S94, 2001.
Tsugeno et al., "A Proton-Pump Inhibitor, Rabeprazole, Improves Ventilatory Function in Patients with Asthma Associated with Gastroesophageal Reflux," *Scand J Gastroenterol.* 38:456-461, 2003. (Abstract only.).
Tsuji et al., "Biodegradable Stents as a Platform to Drug Loading," *International Journal of Cardiovascular Interventions* 5:13-16, 2003.
Unal et al., "Effect of Botulinum Toxin Type A on Nasal Symptoms in Patients with Allergic Rhinitis: A Double-blind, Placebo-controlled Clinical Trial," *Acta Oto-Laryngologica 123*(9):1060-0163, Dec. 2003.
UNSW Embryo-Respiratory System [online] Embryology, 2007, [retrieved on Dec. 10, 2007]. Retrieved from the internet: (URL: http://embryology.med.unsw.edu.au/Refer/respire/select.htm).
Urologix, Inc., "Cooled ThermoTherapy™," 2012, retrieved on Mar. 3, 2005 from URL=http://www.urologix.com/cllinicians/cooled-thermotherapy.php, 2 pages.
Urologix, Inc., "CTC Advance™ Instructions for Use," Targis® System Manual, 2010, 8 pages.
Van Boxem TJM, et al., "Tissue Effects of Bronchoscopic Electrocautery," *Chest 117*(3):887-891, Mar. 1999.
van der Velden et al., "Autonomic Innervation of Human Airways: Structure, Function, and Pathophysiology in Asthma," *Neuroimmunomodulation* 6:145-159, 1999.
Vasilotta, P. I. et al., "I-R Laser: A New Therapy in Rhino-Sino-Nasal Bronchial Syndrome with Asthmatic Component," American Society for Laser medicine and Surgery abstracts, date unknown, p. 74.
Verhein et al., "Neural Control of Airway Inflammation," *Current Allergy and Asthma Reports 9*:484-490, 2009.
Vincken et al., "Improved health outcomes in patients with COPD during 1 yr's treatment with tiotropium," *Eur. Respir. J.* 19: 209-216, 2002.
Vorotnev et al., "Treatment of Patients with Chronic Obstructive Bronchitis Using Low Energy Laser at a General Rehabilitation Center," *Therapeutic Archive* 3:17-19, 1997. (+ English translation, 4 pages.).
Wagner et al., "Methacholine causes reflex bronchoconstriction," *J. Appl. Physiol.* 86:294-297, 1999.
Wahidi et al., "State of the Art: Interventional Pulmonology," *Chest 131*:261-274, 2007.
Wayne Mitzner, "Airway Smooth Muscle the appendix of the Lung," American Journal of Respiratory and Critical Care Medicine, 2004, 169, 787-790.
Wayne Mitzner, "Bronchial Thermoplasty in Asthma," Allergology International, 2006, 55, 225-234.
Weaver, "Electroporation: A General Phenomenon for Manipulating Cells and Tissues," *Journal of Cellular Biochemistry 51*(4):426-435, Apr. 1993.
Wechsler, M.E., "Bronchial Thermoplasty for Asthma: A Critical Review of a New Therapy,", *Allergy and Asthma Proceedings 29*(4):1-6, Jul.-Aug. 2008.
Wiggs B.R. et al., On the Mechanism of Mucosal Folding in Normal and Asthmatic Airways, J. Appl. Physiol., Dec. 1997, 83(6), 1814-1821.
Wilson, K.C., et al., "Flexible Bronchoscopy: Indications and Contraindications," UpToDate, Nov. 12, 2010 <www.uptodate.com> [retrieved Sep. 30, 2012], 15 pages.
Wilson, S. R. et al., Global assessment after bronchial thermoplasty: the patient's perspective, Journal of Outcomes Research, 2006, vol. 10, pp. 37-46.
Wirtz et al., "Bilateral Lung Transplantation for Severe Persistent and Difficult Asthma," *The Journal of Heart and Lung Transplantation 24*(10):1700-1703, 2005.
Wizeman, et al., A Computer Model of Thermal Treatment of Airways by Radiofrequency (RF) Energy Delivery, 2007, American Thoracic Society Annual Meeting, p. 1.
Application and File History for U.S. Appl. No. 12/463,304, filed May 8, 2009, inventors Mayse et al.
Application and File History for U.S. Appl. No. 13/245,522, filed Sep. 26, 2011, inventors Mayse et al.
Application and File History for U.S. Appl. No. 13/452,660, filed Apr. 20, 2012, inventors Mayse et al.
Application and File History for U.S. Appl. No. 13/452,664, filed Apr. 20, 2012, inventors Mayse et al.
Application and File History for U.S. Appl. No. 13/452,648, filed Apr. 20, 2012 inventors Mayse et al.
Application and File History for U.S. Appl. No. 13/452,655, filed Apr. 20, 2012 inventors Mayse et al.
Application and File History for U.S. Appl. No. 13/245,537, filed Sep. 26, 2011 inventors Mayse et al.
Application and File History for U.S. Appl. No. 12/372,607, filed Feb. 17, 2009 inventors Hlavka et al.
Application and File History for U.S. Appl. No. 13/523,223, filed Jun. 14, 2012 inventors Hlavka et al.

SYSTEM AND METHOD FOR BRONCHIAL DILATION

CROSS-REFERENCES TO RELATED APPLICATIONS

This application is a continuation of U.S. patent application Ser. No. 13/523,223, filed on Jun. 14, 2012, now U.S. Pat. No. 8,489,192, which is a continuation of U.S. patent application Ser. No. 12/372,607, filed Feb. 17, 2009, now U.S. Pat. No. 8,483,831, which claims the benefit under 35 U.S.C. §119(e) of U.S. Provisional Application No. 61/066,026 filed Feb. 15, 2008, and of U.S. Provisional Application No. 61/049,605 filed May 1, 2008. Each of these applications is incorporated herein by reference in its entirety.

TECHNICAL FIELD

This document pertains generally to medical devices, and more particularly, but not by way of limitation, to systems and methods for bronchial stimulation.

BACKGROUND

Obstructive pulmonary disease, including asthma, emphysema, or chronic bronchitis, afflicts more than 25 million individuals in the United States and accounted for over 17 million physician office visits in the mid 1990's. Current estimates for the total cost of these diseases are in excess of $20 billion. These diseases are increasing in prevalence due to myriad causal factors, but principally driven by smoking.

While a chronic disease, the hallmark of asthma is acute episodes of difficulty breathing created by an acute constriction of smooth muscles lining the bronchi (the passage ways for air in the lungs), reducing the diameter of the airway and increasing the resistance to air flow. Bronchial constriction in asthma is "reversible" in that the acute constriction can be reversed by bronchodilation medication or by the passage of time (after removal of the irritant that elicited the constriction). However, asthma chronically exhibits itself as inflammation, hypertrophy, or hyper-excitability of the smooth muscles.

Emphysema and chronic bronchitis are different diseases than asthma, but can be related by the same causal factor and concomitant appearance in the same or similar individuals. Both emphysema and chronic bronchitis are predominantly caused by smoking and usually both exist in the same individual, hence they can be lumped together under the umbrella term Chronic Obstructive Pulmonary Disease (COPD). However, the diseases are very different and manifest themselves quite differently. While most subjects exhibit some amount of both diseases, a subject can be categorized by which condition is predominant in the subject's anatomy.

In emphysema, long term exposure to smoke or other noxious substances can result in a primary breakdown of the lung parenchyma (alveoli, etc.). Normal fine alveoli can break down and form large open "holes" (bullea), which in turn can result in reduced surface area for gas exchange, sapping of inhaled air flow from healthy lung tissue, or reduced anchoring of bronchi that can result in airway collapse.

In chronic bronchitis, irritation of the bronchi can result in inflammation, hypertrophy, or constriction of the smooth muscles lining the bronchi, or excessive mucus production that can clog the bronchi. While the smooth muscle contraction in chronic bronchitis is not as "reversible" as that exhibited in asthma, there is usually a significant degree of reversibility and bronchodilator medications can be used as a first line of therapy.

Overview

Chronic bronchitis and asthma can both exhibit airway smooth muscle constriction resulting in airway constriction. The present inventors have recognized, among other things, that bronchodilation medications can be used as a front lines therapy, but are far from optimal treatments, as the efficacy of bronchodilation medications can be limited and subject compliance is often poor between episodes of exacerbation. Further, the present inventors have recognized that inhalers are difficult to use properly and are especially difficult for the elderly (e.g., COPD) and children (e.g., asthma) to use optimally. Thus, the present inventors have recognized that a system or method configured to chronically dilate the bronchi such as by decreasing, inhibiting, or eliminating smooth muscle contraction would be beneficial for many subjects.

An implantable signal generator can be configured to generate a blocking signal to be delivered to at least a portion of a bronchus. The blocking signal can be configured to inhibit nerve traffic both to and from the lungs, to relieve bronchial smooth muscle contraction, and to inhibit cough. The implantable signal generator can be communicatively coupled to a processor configured to control delivery of the blocking signal, using received information about an indication of cough, to inhibit cough.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
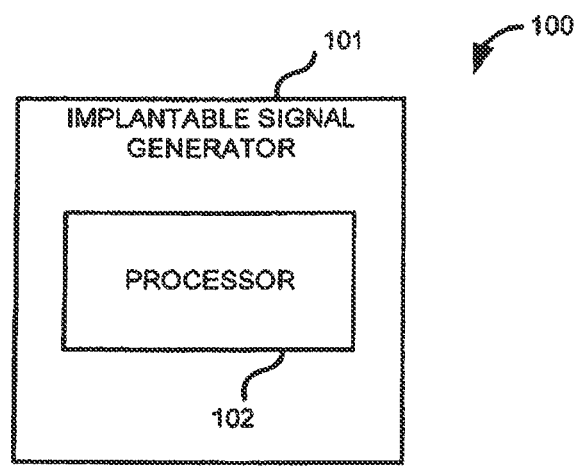
FIG. 1 illustrates generally an example of a system including an implantable signal generator and a processor.

The present inventors have recognized, among other things, a system and method for chronically dilating the bronchi, such as by decreasing, inhibiting, or eliminating smooth muscle contraction.

General Anatomy

In general, the peripheral nervous system can be divided into the somatic nervous system, the enteric nervous system, and the autonomic nervous system. The autonomic nervous system includes autonomic sensory neurons, integrating centers in the central nervous system (e.g., the brain), and autonomic motor neurons. A continual flow of nerve impulses from autonomic sensory neurons in visceral organs (e.g., afferent nerves) and blood vessels propagate into integrating centers in the central nervous system. Further, impulses in autonomic motor neurons (e.g., efferent nerves) can propagate to various effector tissues. This interaction between afferent and efferent propagation regulates the activity of smooth muscles and glands throughout the body.

Autonomic motor neurons have two principal branches: the sympathetic division and the parasympathetic division. Many organs have dual innervation from each of the branches. In general, nerve impulses from one division stimulates the organ to increase its activity (excitation), and impulses from the other division decrease the organ's activity (inhibition).

The balance between sympathetic and parasympathetic activity is termed "autonomic tone" and establishes the status of the organ. The balance is regulated by the hypothalamus, which typically turns up sympathetic tone while simultaneously turning down parasympathetic tone, and vice-versa.

High sympathetic tone supports body functions that support vigorous activity such as increased heart rate, increased blood pressure, etc. High parasympathetic tone supports "rest and digest" functions and has the opposite effect of sympathetic tone. Classically, human airway dilation was considered to be driven by the activation of the sympathetic division. However, other theories suggest that human airway smooth muscle is largely devoid of sympathetic innervation, and that dilation is derived from a different type of parasympathetic nerve.

Most parasympathetic nerves are termed "cholinergic" due to their use of the chemical acetylcholine during firing. Most sympathetic nerves are termed "adrenergic" due to their use of adrenal gland substances during firing. However, additional species such as non-cholinergic, non-adrenergic parasympathetic nerves exist.

The distribution and function of parasympathetic-cholinergic nerves is consistent across species. By contrast, the distribution and function of sympathetic and non-cholinergic parasympathetic innervation of airway smooth muscle varies considerably between species. Human airway smooth muscle is largely devoid of sympathetic adrenergic innervation. Non-adrenergic, non-cholinergic neurotransmitters (likely derived from the parasympathetic nerves) mediate the relaxations induced by the only demonstrably functional relaxant innervation of human airway smooth muscle.

In cats, guinea pigs, and ferrets, non-cholinergic parasympathetic transmitters are not co-released with acetylcholine from a single population of postganglionic parasympathetic nerves. Rather, an anatomically and functionally distinct parasympathetic pathway regulates non-adrenergic, non-cholinergic relaxations of airway smooth muscle. Reflexes differentially regulate the cholinergic and non-cholinergic nerves. Further, the parasympathetic innervation of human airways can be similar to that of cats and guinea pigs.

Both afferent and efferent parasympathetic nerves to the lungs derive from the vagus nerves at or near the pulmonary plexuses. The vagus nerves generally run roughly parallel to or lateral to the esophagus and trachea, while the plexuses are in turn further lateral than the vagi. The plexuses lie on or near the main bronchi near their bifurcation, and the nerves follow the branching of the bronchial tree within the lung parenchyma. Anantomists recognize both anterior and posterior plexuses (or equivalently the ventral and dorsal aspects). However, the anterior/ventral pulmonary plexus can be quite minor compared to the posterior/dorsal plexus. Further, the sympathetic innervation of the lungs pass through the pulmonary plexuses.

Basic Cholinergic Tone

Generally, airway parasympathetic nerves are tonically active during tidal breathing and typically produce a stable, readily reversible baseline obstruction of the airways reflecting opposing influences of contractile and relaxant airway parasympathetic nerves acting on airway smooth muscle.

Constriction of the smooth muscle by activation of efferent parasympathetic nerves can obliterate the lumen of small bronchi and bronchioles, markedly increasing airway resistance in larger, cartilaginous airways. Conversely, bronchodilation can be induced by withdrawing ongoing parasympathetic activity.

Sensory input from the lungs (e.g., via afferent nerves) can play a significant role in the creation of basal tone. Further, deregulation of basal tone, such as that seen in bronchitis or asthma, can originate from altered afferent signaling. A recurring presence and level of baseline tone in the airways can imply the existence of a "set point" for smooth muscle contraction. In certain examples, a withdrawal or augmentation of tone can be achieved in response to physiological or pathophysiological stimuli. Alterations in afferent or efferent nerve function can contribute to airway hyperresponsiveness and airway obstruction in diseases such as asthma or COPD.

In an example, cholinergic nerve activity in the airways can depend on input from afferent (e.g., mechanically sensitive) nerve fibers innervating the intrapulmonary airways and lungs. In certain examples, unilateral or bilateral severing of the afferent (sensory) nerves at the vagus can lead to a decrease in pulmonary resistance, indicating airway dilation.

In certain examples, such as during extreme circumstances (e.g., aspiration of foreign body, near drowning, trauma to the chest wall, etc.), a reflex bronchospasm may confer some physiologic benefit. Additionally, cholinergic tone may serve to minimize the work of breathing under the full variety of breathing states in a healthy individual (e.g., rest, exercise, etc). Further, afferent nerve signaling can be important for the maintenance of other functions, such as cough or mucus clearance. However, under non-extreme circumstances, the complete abolition of smooth muscle tone appears to have little or no physiological downside in a healthy individual. Moreover, in a diseased individual suffering from an obstructive disorder, the complete abolition of smooth muscle tone should be uniformly beneficial

Vagotomy

Generally, blocking the vagal nerves, such as by administering atropine sulfate to block postganglionic cholinergic pathways, by cooling of the nerve, or other blocking of the vagal nerves can result in dilation of the airways. Alternatively, surgical transaction of the vagus nerves can serve the same purpose. Historically, high vagal transection (in the neck region) has been used to treat asthma and COPD with some success. However, since the vagus nerve controls many body functions and organs other than the lungs, surgical transaction of the vagus carry significant complications and has not been adopted.

In a different example, lung transplant recipients can have denervated lungs while their vagus nerves are intact. In these subjects, bronchial diameters can be 150-200% of their normal pre-transplant bronchial diameter. While surgical pulmonary denervation can be an effective therapy for asthma or chronic bronchitis, the effect is typically short lived. The parasympathetic ganglia are typically located within the airways themselves. Generally, within the reimplanted lung, preganglionic fibers degenerate, but ganglia and undivided postganglionic fibers do not. In these instances, because the regenerating preganglionic axons are located only a few centimeters from the line of division, reinnervation can occur rapidly. In certain examples seen in animal models, pulmonary reinnervation can occur within a short period of time (e.g., three months), re-establishing autonomic tone.

Notably, other potentially beneficial side effects can be seen in subjects having denervated lungs. For example, mucus production can be decreased, and cough can be suppressed. In other examples, the sensation of dyspnea can be suppressed.

The present inventors have recognized, among other things, that a chronic, minimally invasive, and reversible system and method can be provided to increase the bronchial diameter of a subject. Further, the present inventors have recognized that while therapy can be directed toward the vagus nerves, there are benefits to directing the therapy more distally, toward the pulmonary parasympathetic nerves, thus limiting the effect to only the lungs and avoiding complications to other organs.

Mediastinoscopy

The mediastinum includes the region in mammals between the pleural sacs containing the heart and all of the thoracic viscera except the lungs. The mediastinum can be accessed using a minimally invasive procedure, such as mediastinoscopy or videomediastinoscopy. These minimally invasive procedures can generally be used to biopsy many of the lymph nodes in this region to aid in the staging determination of various cancers, and can generally be regarded as "day surgeries" having minimal morbidity and fast recovery.

In an example, mediastinoscopy can allow access to the trachea and to the main bronchi distal to the bifurcation. Access can be initiated at the suprasternal notch where dissection can be carried out down to the trachea. The plane of the pre-tracheal fascia can be used to carry the dissection down to the carina (bifurcation of the main bronchi). In another example, the Chamberlain procedure can allow access to the hilar areas of the lungs, e.g., using an initial incision at the 3rd intercostal space.

Mediastinoscopy can be performed by a thoracic surgeon with the subject under general anesthesia. While a host of large vascular structures run through this area, the procedure is generally safe and is the gold standard for lymph node biopsies, commonly having reported morbidity and mortality rates of 0.6% and 0.2%, respectively.

The pulmonary nerves located on the anterior and posterior aspects of the bronchi are available for therapy using the minimally invasive mediastinoscopic approach to the main bronchi.

Video-Assisted Thoracic Surgery

Mediastinoscopy typically does not expose the distal portion of the main bronchi or the dorsal aspect of the main bronchi. Thus, the present inventors have recognized that it may be advantageous to use other surgical techniques to access the bronchi.

In an example, video-assisted thoracic surgery (VATS) can be used to access structures on the thoracic wall (e.g., the sympathetic chain running parallel and lateral to the spinal column) or the lung itself (e.g., for a biopsy, wedge resection, etc.). In a VATS procedure, the lungs can be intubated with a bifurcated endotracheal tube, such that each lung can be ventilated independently. Thus, one lung can be ventilated while the other lung is deflated to provide working room in that side of the chest cavity.

In certain examples, one or more ports (typically less than 5) can be placed between ribs for access to the working space between the deflated lung and the intact chest wall. An elongate scope or camera can be inserted, as well as auxiliary tools, in one or more ports. While ports are typically used for convenience (to maintain easy access to insert and withdraw tools), a physical port is not strictly necessary. A port can include a physical port or a small incision between ribs without the physical port.

In an example, during a procedure, a subject can be positioned lying on one side with the upper arm raised overhead, thereby allowing the one or more ports to be placed in the ventral or dorsal portion of the chest wall and allowing the lung to be retracted either dorsally or ventrally. In an example, if a bilateral procedure is desired, the subject can be repositioned to the contralateral side during the procedure. In certain examples, the subject can be positioned in a prone posture so both sides of the chest cavity can be accessed without repositioning the subject. Further, the prone position allows the deflated lung to fall ventrally, naturally exposing the seam between the visceral and parietal pleura at the posterior (e.g., dorsal) aspect of the main bronchi.

In other examples, other endoscopic procedures can be used to implant at least one of an electrode, a lead, or an implantable signal generator.

Therapy

In an example, surgical transection of the pulmonary nerves can abolish tonic smooth muscle tone. However, as discussed above, the duration of the effect can be limited. In certain examples, the duration can be as short as 3 to 12 months before re-innervation can occur.

As a result, several other approaches can be considered. In an example, the pulmonary nerves can be transected at several locations using a series of lesions (e.g., linear or other) created around at least a portion of the circumference of the bronchi. In an example, electrocautery can be used to create one or more linear lesions. In certain examples, two or more lesions can be created, separated by gaps, such as 2 mm to 15 mm gaps.

In other examples, an implant having a bioactive component or coating (e.g., that suppresses neuron growth or regeneration) can be attached or otherwise placed on or around the bronchi to prevent the severed nerves from reinnervating. In certain examples, the coating can be similar to or the same as the coating used on drug coated stents placed in the heart (e.g., paclitaxel or serolimus), which are known to suppress cellular proliferation In an example, an active implantable system, such as an implantable signal generator and lead system, can be provided, portions of which can be placed on or around the bronchi. Because afferent signals from the lungs are typically needed to produce the tonic smooth muscle tone, and because the tone is generally triggered by efferent parasympathetic fibers, substantially inhibiting or blocking nerve signals at the bronchi can serve the dual purpose of blocking both outgoing and incoming signals from the lungs. In this example, afferent signaling into the integrating centers in the central nervous system and outgoing signals to the smooth muscles can both be inhibited, effectively creating a "belt and suspenders" redundancy.

In an example, efferent and afferent parasympathetic and sympathetic nerve signals can be substantially inhibited or blocked at the bronchi. In certain examples, the inhibition or blocking can be accomplished without providing efferent or afferent stimulation (e.g., inducing action potentials) to the sympathetic or parasympathetic nerves at or near the bronchi.

Blocking

In an example, nerve "blocking" can be realized by placing one or more nerve cuffs or other electrodes near the postganglionic ascending afferent pulmonary nerves and postganglionic descending efferent pulmonary nerves on each pulmonary trunk. In other examples, the nerve "blocking" can be realized by placing one or more nerve cuffs on the preganglionic vagus nerves on each pulmonary trunk, or by placing one or more other electrodes (e.g., nerve stimulation patch electrodes, such as an internal or external surface, plunge, or other electrode configuration) on the pulmonary nerve plexus or ganglia. In certain examples, other blocking electrodes can be placed elsewhere within or throughout the upper bronchial tree or trachea, e.g., to further or more finely control the blocking. In an example, one or more leads connecting one or more electrodes to a signal generator can exit the mediastinum through the surgeon's access route and can be tunneled subcutaneously from the suprasternal skin incision to a convenient location for the implanted signal generator.

In an example, the blocking signal can be on the order of 10-5000 Hertz (in some cases higher than 5000 Hertz), 0.1-10 mA, with a pulse width of 50 µs-2 ms. In other examples, other blocking signals having different ranges can be used, or a clamping signal, such as a voltage or current clamping signal, can be applied. In certain examples, the clamping signal can bias a cell such that an action potential can be prohibited.

Duty Cycle

In certain examples, the implantable system can be controlled using a duty cycle. In an example, because the signal generator is implantable, conservation of battery power can be important. Various duty cycling schemes can be applied to conserve power. In certain examples, the implantable system can include the ability to program electrostimulation duty cycle (e.g., on a percentage basis, such as from 1% to 100%; such as "on" for 5% of the stimulation period (1/frequency), on a recurring cycle duration basis, such as "on" for x of y seconds, such as "on" for 1 second out of 100 seconds up to "on" for 100 seconds out of 100 seconds, or other time measures, such as minutes, hours, or days).

Physiologic Adaption Avoidance and/or Functional Allowance

In an example, the implantable system can be programmed to pause therapy delivery for a variable amount of time and then have therapy resume, or to modify/modulate one aspect of therapy delivery, such as changing the stimulation frequency or duty cycle, in order to prevent the pulmonary system from adapting to the therapy stimulation sequence and to maintain therapy efficacy. In an example, the implantable system can be configured to provide a frequency hopping or varying frequency stimulation for anti-habituation.

In an example, the implantable system can activate, deactivate, increase, or decrease the blocking effect in response to one or more physiological or other parameter. In certain examples, the blocking can be increased or decreased in response to detected physical activity (e.g., physical activity sensed using a sensor, such as an accelerometer coupled to the implantable signal generator), the blocking can be activated or deactivated in response to sensed physiological parameters (e.g., a bronchial diameter decrease sensed using a sensor, such as a strain gauge, an impedance sensor, or other electrical, mechanical, or other sensor, etc.).

In an example, the implantable system can modulate the therapy based on a circadian or other rhythm of the subject (e.g., sensed using a sleep sensor, time of day, clock, or other sensor), or the implantable system can modulate the therapy to provide for one or more periods of no therapy (e.g., user selected time periods), or by abstaining from providing therapy to one side of the bronchi while the other side receives therapy or vice versa, for example, to allow the autonomic system to provide general pulmonary maintenance, such as coughing, mucus clearance, mucus production, or other physiological response. For example, COPD subjects can be particularly susceptible during the early morning hours to exacerbation. As such, maximum therapy can be desirable during this time period.

In other examples, the implantable system can be configured to deliver therapy during time periods of peak constriction or discomfort. Many subjects have identifiable periods of maximum constriction or discomfort, such as in the morning following sleep, in the evening before sleep, or during one or more other time periods. In an example, the implantable sensor can include a sleep sensor or posture sensor configured to detect and to inhibit therapy during sleep, or configured to provide therapy following the detected cessation of sleep. In an example, periods of maximum therapy or no therapy can be configured using population data, or can be configured using specific subject data. In an example, the implantable system can initially be configured using population or clinical data, and then can be adjusted according to individual subject needs.

For example, if a specific subject commonly reports waking at or near a specified time during sleep feeling short of breath or having discomfort, the implantable system can be configured to provide therapy around the reported time, relieving the discomfort of the subject. Further, therapy can automatically be provided following a detected cessation of sleep. If the detected cessation is during a normal sleep time of the subject, indicating that airway restriction or subject discomfort caused the subject to wake, therapy can be provided.

In an example, the implantable system can be configured to cease therapy during periods where therapy is not needed. In an example, the periods can be identified using information from the subject, from a population, or the periods can be user-specified. For example, certain subjects feel little to no constriction or discomfort during the afternoon. In this example, to conserve battery life, or to allow normal physiological response of the subject to resume, therapy can be prohibited during the identified period.

In other examples, therapy can be switched off during periods of exacerbation, such as COPD exacerbation. In an example, COPD exacerbation can include a worsening of COPD symptoms beyond normal day-to-day variation. In an example, exacerbation can be sensed using one or more physiological parameters configured to monitor symptoms of COPD, such as breathlessness, cough, sputum or mucus production, color, or thickness, wheezing, thoracic pressure (e.g., chest tightness, pressure, or pain, etc.), or one or more other symptoms. In other examples, the implantable system can receive one or more other indicators of exacerbation, such as hospitalization, or one or more other user inputs indicating exacerbation.

In an example, therapy can be switched off during hospitalization, or during one or more other physiological or time periods specified by a clinician. Hospitalization can be manually input, or automatically determined using medical record data or one or more other source of medical information.

Cough

In an example, inhibiting nerve traffic to one or more lung, from one or more lung, or both to and from one or more lung along one or more of the bronchi can block, inhibit, or reduce the urge of a subject to cough, for example, by reducing the ability of one or more of the bronchi to contract, or by blocking afferent signals from receptors responsive to gas, toxins, foreign matter, etc.

In an example, the implantable system can include one or more sensor (e.g., cough sensor) or input configured to receive an indication of acute or chronic cough, such as a pressure sensor, a respiration sensor, a sound sensor, an activity sensor, an impedance sensor, a phrenic nerve input, or other sensor configured to detect or receive an indication of cough. In an example, the pressure sensor can be configured to detect a change in pressure in a body (e.g., airway, thorax, etc.) indicative of a cough. In an example, the respiration sensor (e.g., tidal volume sensor, minute ventilation (MV) sensor, etc.) can be configured to detect a change in respiration indicative of a cough. In an example, the sound sensor (accelerometer, microphone, etc.) can be configured to detect a change in sound indicative of a cough. In an example, the activity sensor (e.g., accelerometer, etc.) can be configured to detect a vibration, motion, or other activity of a subject indicative of a cough. In an example, the impedance sensor can be configured to detect impedance (e.g., a change in impedance) indicative of fluid (e.g., mucus, etc.) buildup, accumulation, or a change in consistency of the lungs, bronchi, or airway indicative of a likely period of cough, or mucas buildup. In an example, one or more electrodes can be used to sense or detect phrenic nerve (or other nerve) activity indicative of cough.

In an example, upon sensing or detecting acute or chronic cough, the implantable system can be configured to inhibit nerve traffic along one or more of the bronchi, blocking, inhibiting, or reducing the ability of a subject to cough. In other examples, the implantable system can be configured to deliver therapy upon sensing or detecting a series of coughs, or coughing or a rate of coughing over a specified (e.g., user specified) period of time (e.g., 1 minute, 5 minutes, etc,). In an example, the inhibition can continue for a period of time (e.g., a time period established by a clinician), after which, the therapy can cease, only to resume if the coughing continues or begins again following therapy.

In other examples, the implantable system can include one or more user-inputs configured to receive a user indication of cough, or a user-indicated cough event (e.g., a subject, clinician, or other caregiver indication of cough, a subject-indicated, clinician-indicated, or other caregiver-indicated cough event, etc.). In an example, the implantable system can be configured to receive input from an external device configured to receive input from the user. In an example, the external device can include a subject control. As the subject experiences a cough or series of coughs, the subject can provide a request, using the external device, to the implantable system to provide blocking therapy. In other examples, the external device can include a medical device programmer, or other clinician operated device. As the subject is being treated for cough (e.g., chronic cough), the clinician or other caregiver or user can provide a request to the implantable system, using the external device, to provide blocking therapy to treat the coughing. Upon receiving the request or indication of cough, the implantable system can deliver the blocking therapy, inhibiting nerve traffic both to and from the lungs, treating the cough.

In an example, after sensing or detecting cough, or upon receiving a user indication of cough, the blocking therapy can be delivered. In an example, the blocking can be delivered for a period of time and then stopped to ascertain whether the coughing or cough episode has ceased. In other examples, the blocking can be delivered until the sensing or detecting an indication of cough has detected a cessation of cough, or the blocking can be delivered until a user identified cessation of cough is received. If coughing continues, then the blocking signal can be resumed.

In other examples, the implantable system can be configured to allow cough (e.g., by stopping therapy), such as for mucus, sputum, or other matter clearance during one or more therapy programs. Further, by blocking or inhibiting neural traffic on at least a portion of the bronchi, mucus production can be inhibited or reduced by blocking efferent signals configured to trigger mucus production.

Pulmonary Toilet

In an example, certain subjects (e.g., having chronic bronchitis, etc.) can benefit from productive cough, by allowing mucus or other foreign matter to escape the lungs or bronchi. In an example, the mucus or other foreign matter can be detected, such as by using a mucus or other sensor. In other examples, a user (e.g., a subject, a clinician, or other caregiver or user) can be configured to provide a normal or other period of time where no therapy is to be delivered (e.g., no blocking signal is to be provided to the subject), to allow for clearance of mucus or other matter.

In an example, the time period can include a daily, hourly, or other normal or other period configured to allow a time for normal pulmonary maintenance, or to allow for the clearance of mucus or other matter in the absence of, or in conjunction with, detected mucus or other foreign matter buildup.

In an example, the time period can include a preset daily period (e.g., 15 minutes, 1 hour, etc.) occurring at a specific time of day (e.g., 8 AM, 10 PM, etc.). In other examples, the time period can include a period of time after the subject has woken from sleep. In certain examples, a sleep sensor, subject activity or posture sensor, or other sensor can be used to detect a sleep or awake state of the subject.

In other examples, the time period can include a more regular interval, such as "off" for 15 minutes and "on" for 45 minutes, "off" for 5 minutes and "on" for 1 hour, etc.

Hyperinflation

In an example, the implantable system can be configured to detect and apply therapy during periods of hyperinflation.

Hyperinflation occurs as inhalation increases faster than exhalation. In a healthy subject, as inhalation increases (e.g., during activity), exhalation increases to expel the increased volume of air. However, if inhalation increases and exhalation does not increase, the subject's respiration baseline approaches the maximum respiration capacity of the lungs, leaving the subject short of breath and starved of oxygen. By dilating the bronchi, more air can be allowed to escape, increasing the ability of the subject to exhale.

In an example, hyperinflation can be detected by a combination of factors, such as an increase in subject activity (e.g., indicative of an increased respiratory need), an increase in breathing frequency, or a decrease in respiration volume. Once hyperinflation is detected, therapy can be provided or increased to increase the diameter of the bronchi, opening the airway.

Titrate Therapy with Drug Stimulation

In an example, the implantable system can be configured to provide the blocking signal in conjunction with drug stimulation. Many COPD subjects take a drugs (e.g., spiriva, etc.) configured to prevent bronchospasm (narrowing of the airway), or to provide airway dilation. In an example, the implantable system can be configured to work with the drug stimulation to increase total efficacy of therapy.

For example, many subjects taking anticholinergic agents, such as spiriva, do so at set times (e.g., daily in the morning, etc.). Using the dosage and instructions for use, blocking therapy can be provided as the effects of the anticholinergic begin to decrease, thereby extending the total effect of therapy.

In an example, if a subject receives a dose of an anticholinergic agent in the morning, the effect (e.g., measured forced expiratory volume (FEV)) increases initially, peaks, then gradually falls off. In an example, as the effect of the drug begins to decline, blocking therapy can be provided to extend the total effect of therapy (e.g., by increasing the total expiratory volume). In an example, once the subject is determined to be asleep, or once the subject is instructed to receive another dose of the anticholinergic agent, blocking therapy can be ceased.

Hyperplasia and Hypertrophy

Many COPD subjects have an enlarged, thick, or bulked bronchi reducing the diameter of the airway due to hyperplasia (cell multiplication), hypertrophy (cell enlargement, muscle bulk), or both. In order to achieve maximum dilation of the bronchi, the muscles of the bronchi must be at rest, or debulked. In an example, providing a blocking signal and relieving smooth muscle contraction can relax the muscles of the bronchi, over time, leading to a debulking of tissue or a loss of smooth muscle tone.

In an example, a narrow bronchial passage can be detected using a detected pressure through the airway, using a detected volume of air through the airway, or using a relationship between both. In certain examples, pressure can be detected in the bronchi. In other examples, other surrogates can be used, such as airway pressure in other parts of the respiratory system. In an example, an airway pressure or volume can be detected using temperature sensors, detecting an air temperature drop along a pathway.

In an example, once a narrow bronchial passage has been detected, therapy can be provided to relieve smooth muscle contraction. In certain examples, the blocking therapy can be combined with one or more other debulking techniques, such as ablation, etc.

Pulse Generator

In an example, an implantable signal generator can be configured to receive information from at least one sensor or other system component and modulate the blocking signal using the received information. In an example, the system component can include a component, such as a processor or other sensor or module, capable of generating an internally generated event, such as a clock or other marker or trigger. In other examples, the sensor can include one or more other physiologic or other sensors configured to sense physiologic or other information from the subject.

Programmer

In an example, the system can include a clinician programmer configured to be communicatively coupled (e.g., wirelessly coupled) to at least a portion of the implantable system, such as the implantable signal generator, etc. In an example, the clinician programmer can be configured to receive information from, or send information to, the implantable signal generator. In other examples, the clinician programmer can allow a clinician or other user to program or otherwise send instructions to the implantable signal generator.

Subject Actuator

In an example, the system can include a subject programmer or subject actuator configured to be communicatively coupled to at least a portion of the implantable system. In an example, the subject programmer can provide for communication between the clinician programmer and the implantable system, such as by acting as a repeater. The subject programmer can be configured to communicate locally with the implantable system, and remotely with the clinician programmer.

In an example, the subject programmer can be configured to allow a subject to control, alter, or otherwise change at least one operating characteristic of the implantable system. In an example, the subject can turn the implantable system on or off using the subject programmer or subject actuator. In other examples, the subject programmer can be configured to communicate information to or from the subject to a clinician or the implantable system.

Battery

In other examples, the implantable system can include one or more other aspects, such as a primary or secondary cell battery system having various charging or re-charging capabilities. The battery system can include a primary cell, a secondary cell (e.g., rechargeable), or other topology. The secondary cell topology can include or be coupled to a charging system, such as an inductively coupled, acoustically coupled, photonically coupled, or other coupled charging system.

Battery Charger

In an example, the system can include a battery charger. The battery charger can include implantable components included in or coupled to the implantable system, external components, or a combination of implantable and external components. In an example, the battery charger can be configured to wirelessly charge (e.g., inductively, etc.) the implantable system. In an example, the implantable signal generator can be implanted subcutaneously outside of the thorax, e.g., accessible for maintenance, battery charging or replacement, or for communication outside of the body.

Lead/Electrode

In an example, implantable system can include a multi-lead or multi-lead multi-channel system. The multi-lead system can include one or more leads, each having one or more electrodes. In certain examples, the leads or the electrodes can be electrically coupled, or can be electrically independent from each other. In other examples, the leads or electrodes can be electrically (e.g., directly, such as through a lead) coupled to an implantable signal generator, or the leads or electrodes can be wirelessly coupled to the implantable signal generator, such as by using one or more wireless transceivers or communication modules.

For example, a wireless lead can be implanted at the pulmonary nerves and communicate wirelessly with an implantable signal generator. Alternatively, a wireless lead could be placed endo-bronchially (without surgery) and communicate with an implantable signal generator.

Telemetry

Further, the implantable system can include a telemetry system, configured to communicate between the implantable system and an external device, such as unidirectionally or bidirectionally. The implantable system can be configured communicated wirelessly with the external device, such as by inductive, RF, or other telemetry. The communication can be configured to transfer information between the implantable system and the external device, such as one or more of programming information, physiological information, or other instructions or information.

Example Procedural Description and Steps

1. Intubate subject with a bifurcated endotracheal tube.
2. Position subject in lateral recumbent position with arm raised over head, exposing both anterior and posterior chest walls on operative side.
3. Ventilate subject on non-operative side only.
4. Make skin incisions and place ports using blunt dissection at desired locations on the anterior and posterior chest wall, typically from the $4^{th}$ through $8^{th}$ rib interspaces.
5. Lung will collapse spontaneously once chest wall is violated and ET tube is allowed to vent on operative side.
6. Insert thorascope and auxiliary tools through ports.
7. A combination of subject positioning (slightly rolled forward) and retraction may be used to cause the lung to roll anteriorly, exposing the reflection of the parietal and visceral pleura.
8. Use careful blunt and sharp dissection to incise the reflection of the pleura at the bronchus.
9. Bluntly dissect connective tissue to isolate the bronchus at a distance approximately 1 to 4 cartilaginous "rings" from where the bronchus enters the lung parenchyma.
10. Care must be taken to avoid damage to the aorta or azygous vein (depending on side of surgery), pulmonary artery, and pulmonary vein.
11. Attach cuff electrode (with attached lead) to the dorsal aspect of the bronchus at a distance approximately 1 to 4 "rings" from the lung parenchyma.
   a. Note: alternative electrode configurations may require different attachment techniques.
   b. In the case of a loop electrode, blunt dissection is carried out around the complete circumference of the bronchus. A suture may be passes around the bronchus, which can then be used in turn to pull an electrode around the bronchus.
12. Loop the lead superiorly over the hilum of the lung, being careful not to kink, twist, or apply tension to the lead.
13. The lead may also be tunneled under the pleura for a distance along the inside of the chest wall.
14. At the desired location, typically on the anterior chest wall, the lead may be tunneled between the ribs. On the exterior chest, the led may be tunneled subcutaneously to a desired location for the signal generator, typically near the clavicle or on the abdominal wall.
15. Re-inflate the collapsed lung and reposition the subject to the contralateral side.
16. Place the second electrode and lead analogously to the first.
17. Test each lead for appropriate and correct electrical contact and functioning.
18. Create a subcutaneous pocket for the signal generator at the desired location.
19. Attach both leads and turn on the signal generator.
20. Insert bilateral chest tubes and close all incisions.
21. Chest tubes may be removed approximately 24 hours post operatively once a chest X-ray confirms the absence of clinically significant pneumothorax and/or pleura effusion.

In an example, a subject can be intubated, such as by using a bifurcated endotracheal tube or other appropriate medical instrument.

In an example, the subject can be positioned in a lateral recumbent position with arm raised overhead, exposing both anterior and posterior chest walls on operative side. In other examples, the subject can be positioned in one or more other positions allowing access to the lungs.

In an example, the subject can be operated on a first side only, and can be ventilated on the non-operative side. In an example, skin can be made and ports can be placed using blunt dissection at one or more desired locations on the anterior or posterior chest wall. In an example, the desired locations can be located between the 4th through 8th rib interspaces.

Once the chest wall is violated, the lung can collapse, and the endotracheal tube can be used to provide ventilation on the operative side. Once the lung is collapsed, medical instruments, such as a thorascope or auxiliary tools, can be inserted through the ports.

In certain examples, a combination of subject positioning (slightly rolled forward) and retraction can be used to cause the lung to roll anteriorly, exposing the reflection of the parietal and visceral pleura.

Once exposed, a careful blunt and sharp dissection can be used to incise the reflection of the pleura at the bronchus. From there, connective tissue can be bluntly dissected to isolate the bronchus, e.g., at a distance approximately 1 to 4 cartilaginous "rings" from where the bronchus enters the lung parenchyma. Care must be taken to avoid damage to the aorta or azygous vein (depending on side of surgery), pulmonary artery, and pulmonary vein.

In an example, an electrode, such as a cuff electrode (with attached lead) can be attached to the dorsal aspect of the bronchus at a distance approximately 1 to 4 "rings" from the lung parenchyma. In certain examples, alternative electrode configurations can require different attachment techniques.

For example, in the case of a loop electrode, blunt dissection can be carried out around the complete circumference of the bronchus. A suture can be passed around the bronchus, which can then be used in turn to pull an electrode around the bronchus.

In an example, a lead coupled to the electrode can be looped superiorly over the hilum of the lung, being careful not to kink, twist, or apply tension to the lead.

In certain examples, the lead can also be tunneled under the pleura for a distance along the inside of the chest wall. At the desired location, typically on the anterior chest wall, the lead can be tunneled between the ribs. On the exterior chest, the led may be tunneled subcutaneously to a desired location for the signal generator, typically near the clavicle or on the abdominal wall.

In an example, the collapsed lung can be re-inflated, and the subject can be repositioned to the contralateral side. Once re-positioned, the subject can be operated on the second side, previously non-operative side. Similar steps can be followed to place a second electrode on the second side analogously to the first electrode. Once implanted, each lead for each electrode can be tested for appropriate and correct electrical contact and functioning.

In an example, a subcutaneous pocket can be created for the signal generator at a desired location. Once the pocket is created, and the signal generator is placed, both leads can be attached and the signal generator can be turned on.

In an example, bilateral chest tubes can be inserted and all incisions can be closed. Following a recovery period, (e.g., 24 hours), and successful testing to confirm the absence of clinically significant pneumothorax or pleura effusion (e.g., using a chest X-ray or other method), the chest tubes can be removed.

In other examples, one or more other methods can be used to implant the signal generator and provide one or more electrodes coupled to or proximate one or more of the bronchi.

FIG. 1 illustrates generally an example of a system 100 including an implantable signal generator 101 and a processor 102 coupled to the signal generator 101. In certain examples, the processor 102 can be included in, or can be separate from the implantable signal generator 101. In an example, the processor 102 can include an external component configured to be wirelessly coupled to the implantable signal generator 101.

In an example, the implantable signal generator 101 can be configured to generate a blocking signal to be delivered to at least a portion of a bronchus of a subject. In an example, the blocking signal can be configured to inhibit efferent nerve traffic, afferent nerve traffic, or both efferent and afferent nerve traffic between the central nervous system and at least a portion of the bronchus or a lung. In an example, the blocking signal can be configured to relieve bronchial smooth muscle contraction, and can inhibit cough, e.g., by blocking nerve signals to and from the respiratory anatomy.

In an example, the processor 102 can be configured to receive information about an indication of cough. In certain examples, the information can include information from a user-identified indication of cough, the information can include information from a sensor configured to detect an indication of cough, or the information can include information from both the user-identified indication and the sensor. In an example, the processor 102 can be configured to control delivery of the blocking signal to the at least a portion of the bronchus, e.g., to inhibit cough.

Figure 2:
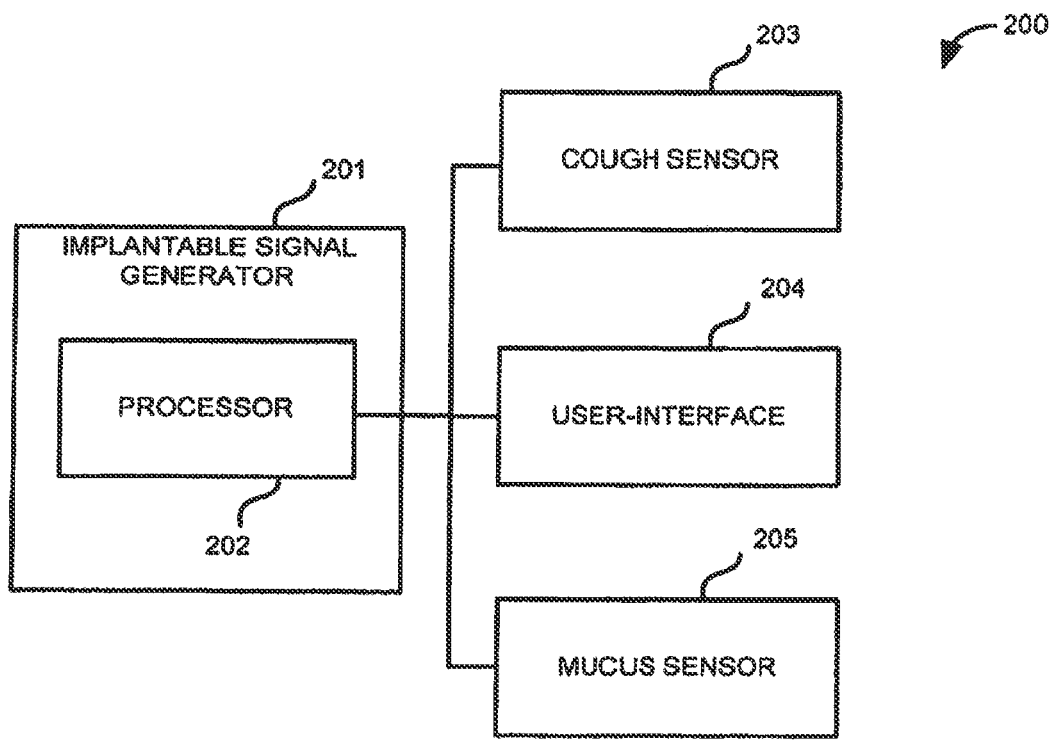
FIG. 2 illustrates generally an example of a system including a cough sensor, a user-interface, and a mucus sensor.

FIG. 2 illustrates generally an example of a system 200 including an implantable signal generator 201 and a processor 202 coupled to the signal generator 201. In certain examples, the system 200 can include at least one of a cough sensor 203, a user-interface 204, or a mucus sensor 205 coupled to the processor 202.

In an example, the cough sensor 203 can include one or more implantable or external sensors configured to detect an indication of cough. In an example, the cough sensor 203 can be configured to detect a cough or an episode of one or more coughs, and to provide information about the detected cough or episode or one or more coughs to at least one of the processor 202 or the signal generator 201.

In an example, the user-interface 204 can include one or more user-inputs configured to receive information from a user (e.g., a subject, a clinician, a caregiver, or other user). In an example, the user-interface 204 can be configured to receive information about an indication of cough from the user, and to provide information about the indication of cough to at least one of the processor 202 or the signal generator 201.

In an example, the user-interface 204 can include a subject-interface, configured to allow the subject to identify an undesired period of cough, e.g., by pushing a button or providing one or more other inputs. In an example, information about the subject-identified undesired period of cough can be provided to at least one of the processor 202 or the signal generator 201.

In an example, the mucus sensor 205 can include one or more implantable or external sensors configured to detect mucus or other matter, or to detect a building or accumulation of mucus or other matter in the lungs or bronchi. In an example, the mucus sensor 205 can include an impedance sensor, or other sensor configured to detect the buildup or accumulation of mucus or fluid in the lungs or bronchi. In an example, the mucus sensor 205 can be configured to provide information about the detected mucus or other matter to at least one of the processor 202 or the signal generator 201.

Figure 3:
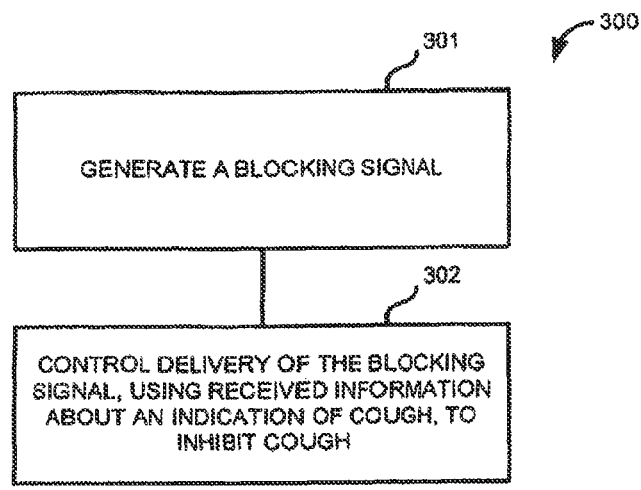
FIG. 3 illustrates generally an example of a method including controlling delivery of a blocking signal to inhibit cough.

FIG. 3 illustrates generally an example of a method 300 including controlling delivery of a blocking signal to inhibit cough.

At 301, a blocking signal can be generated. In an example, the blocking signal is generated using a signal generator, such as the implantable signal generator 101.

At 302, information about an indication of cough is received, and delivery of the blocking signal is controlled, using the received information, to inhibit cough.

Figure 4:
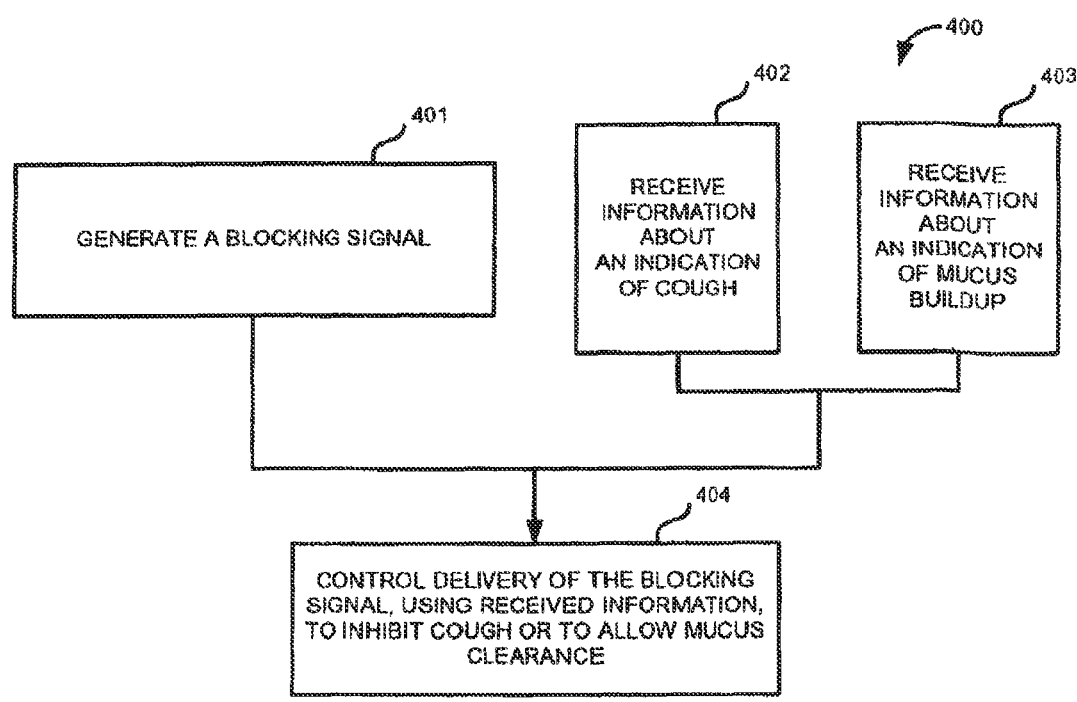
FIG. 4 illustrates generally an example of a method including controlling delivery of a blocking signal to inhibit cough, or to allow mucus clearance.

FIG. 4 illustrates generally an example of a method 400 including controlling delivery of a blocking signal to inhibit cough, or to allow mucus clearance.

At 401, a blocking signal is generated, for example, using a signal generator, such as the implantable signal generator 101.

At 402, information about an indication of cough is received. In an example, the indication of cough can be received from at least one of a cough sensor (e.g., the cough sensor 203 or other sensor configured to detect an indication of cough) or a user-interface (e.g., the user-interface 204 or other user-input configured to receive a user-identified cough indication).

At 403, information about an indication of mucus building is received. In an example, the indication of mucus building can be received from a mucus sensor, such as the mucus sensor 205 or other sensor configured to detect an indication of mucus or fluid accumulation in at least one of a lung or bronchi.

At 404, delivery of the blocking signal can be controlled, using received information, to inhibit cough or to allow mucus clearance. In an example, the delivery of the blocking signal can be controlled using the received information about the indication of cough, about the received information about the indication of mucus buildup, or both. In an example, the controlling the delivery of the blocking signal can include providing the blocking signal to at least a portion of the bronchi if an indication of cough is detected or received. In other examples, the controlling the deliver of the blocking signal can include not providing the blocking signal if an indication of mucus buildup or other fluid or foreign matter is detected or received.

Figure 5:
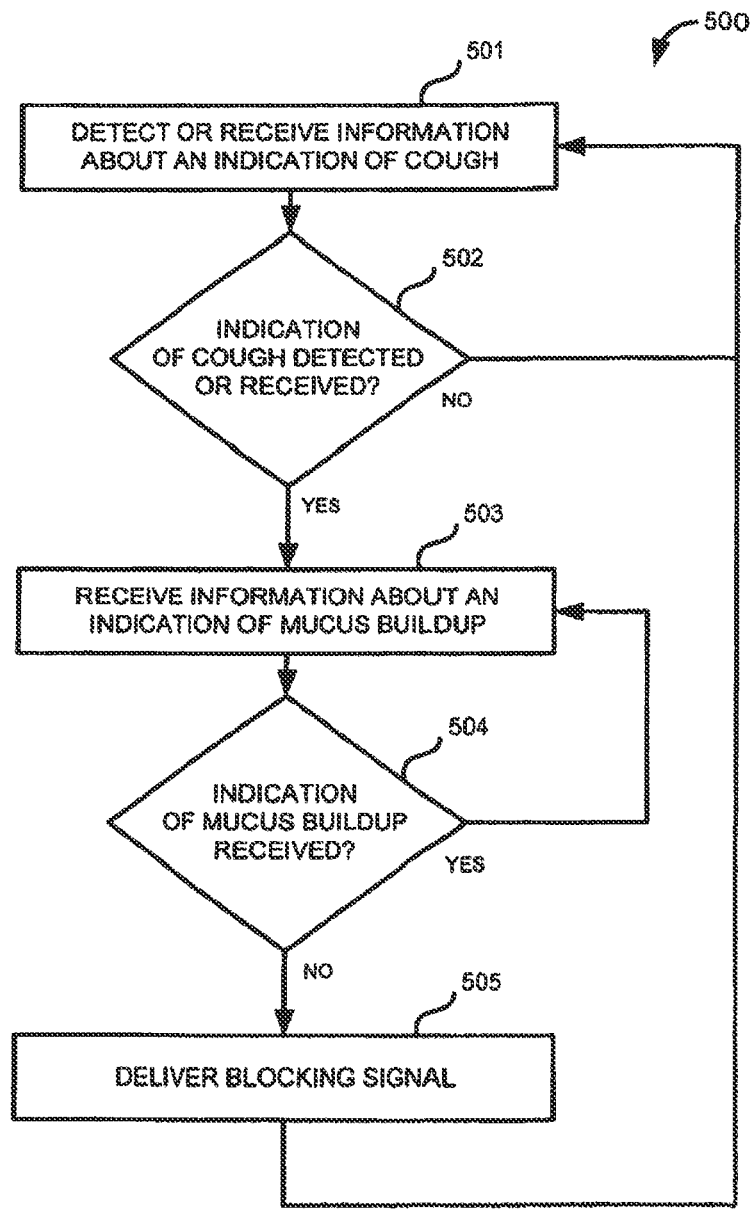
FIG. 5 illustrates generally an example of a method including delivering a blocking signal.

FIG. 5 illustrates generally an example of a method 500 including delivering a blocking signal.

At 501, information about an indication of cough is detected or received. In an example, the information can be detected or received using at least one of a cough sensor (e.g., the cough sensor 203 or other sensor configured to detect an indication of cough) or a user-interface (e.g., the user-interface 204 or other user-input configured to receive a user-identified indication of cough).

At 502, if an indication of cough is detected or received, then, at 503, information about an indication of mucus buildup is received. At 502, if an indication of cough is not detected or received, then process flow returns to 501.

At 504, if the information about the indication of mucus building indicates that mucus has not built up, then, at 505, a blocking signal is delivered configured to inhibit cough. In an example, a blocking signal can be delivered to at least a portion of a bronchus using an implantable signal generator. In an example, the blocking signal can be configured to inhibit nerve traffic both to and from the lungs, relieving bronchial smooth muscle contraction and inhibiting cough. In other examples, the blocking signal can be configured to inhibit mucus production.

At 504, if the information about the indication of mucus building indicates that mucus has built up, then process flow returns to 503. In an example, once the mucus buildup is cleared, e.g., by cough, then the blocking signal can be delivered to inhibit cough. In certain examples, the blocking signal can be ceased for a specified time to allow for mucus clearance, or the blocking signal can be ceased until an indication of mucus or fluid clearance is received using the mucus sensor.

In certain examples, if cough continues, but mucus is not cleared, information can be provided to a user, a clinician, or other caregiver, such as using an alarm or other notification. In other examples, other information, such as the information about the indication of cough or mucus buildup, can be provided.

Figure 6A:
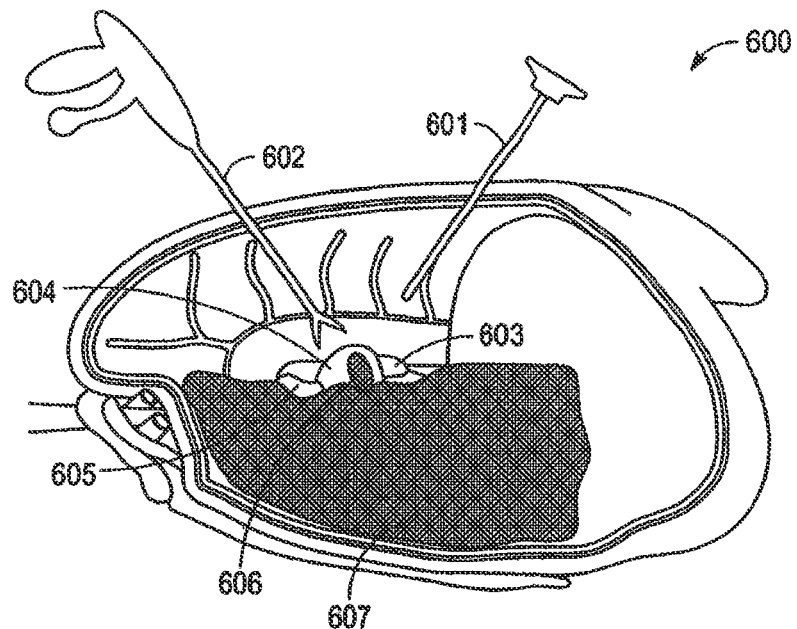
FIGS. 6A-6B illustrate generally structures in a thorax during access.
Figure 6B:
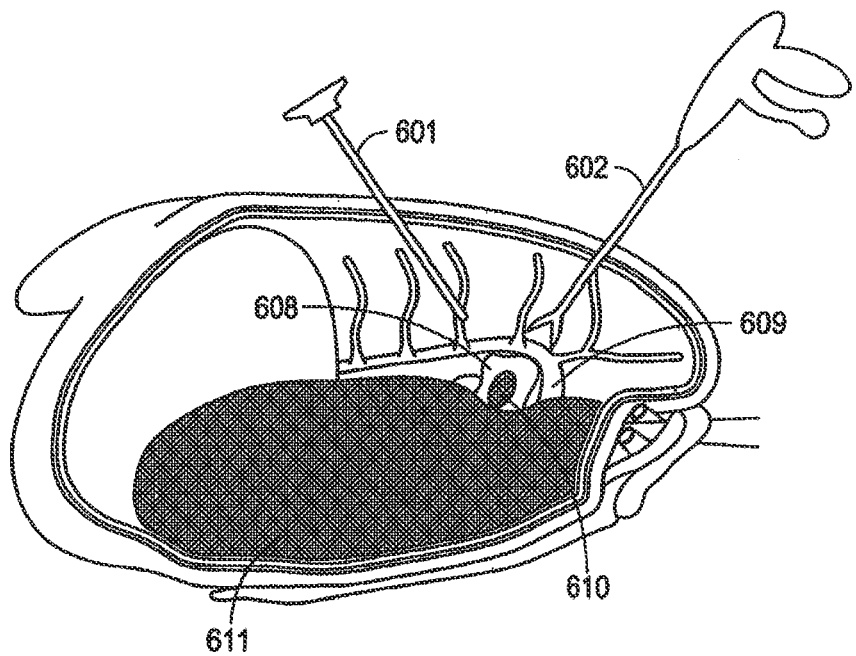

FIGS. 6A and 6B illustrate generally structures in a thorax during access, including an incised pleura at a parietal-visceral reflection. FIG. 6A illustrates a left mediastinum exposure, including a left inferior pulmonary vein 603, a left main bronchus 604, a left pulmonary artery 605, a left posterior pulmonary plexus 606, and a deflated left lung 607. FIG. 6B illustrates a right mediastinum exposure, including a right main bronchus 608, an azygous vein 609, a right posterior pulmonary plexus 610, and a right lung 611.

In these examples, a first instrument 601, such as a fiberscope, a thoracoscope, or other instrument, can enter the thorax, such as into the sixth rib interspace, and a second tool 602, such as a dissection tool or other instrument, can enter the thorax, such as into the fourth rib interspace. In other examples, at least one of the first or second instruments 601, 602, can access the thorax at one or more other locations.

Generally, working between the spine and its associated vascular structure and the deflated lung, an incision in the pleura can be made at the reflection of the parietal pleura and the visceral pleura allowing access to the dorsal aspect of the main bronchi. In the example of FIG. 6A, a descending aorta is close to the spinal column and is left undisturbed. In the example of FIG. 6B, the azygous vein 609 is close to the spinal column and is left undisturbed. In an example, once the dorsal aspect of the main bronchi has been accessed, an electrode (e.g., a cuff electrode, patch electrode, etc.) can be affixed to the dorsal aspect of the main bronchi near where the bronchi enter the lung parenchyma.

FIGS. 7-10 illustrate generally examples of various signal generator implant sites, lead paths, electrode sites, and electrode configurations.

Figure 7:
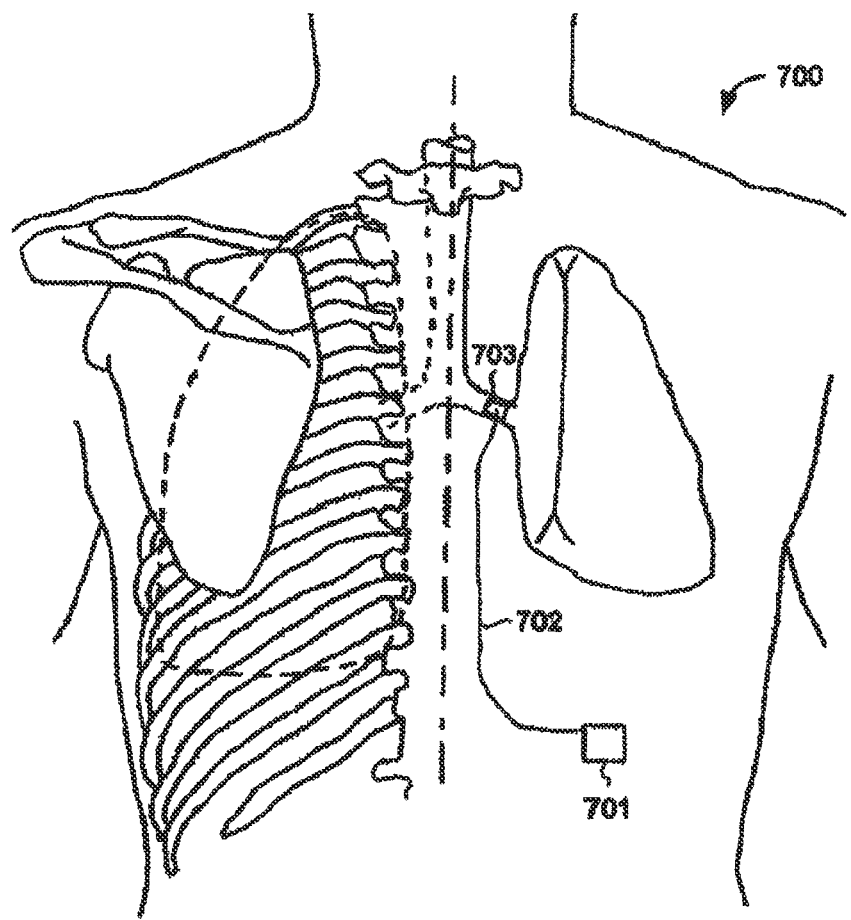
FIGS. 7-10 illustrate generally examples of various signal generator implant sites, lead paths, electrode sites, and electrode configurations.

FIG. 7 illustrates generally an example of a system 700 including an implantable signal generator 701, a lead 702 coupled to the implantable signal generator 701, and an electrode 703 coupled to the lead 702. In this example, the electrode can be affixed to or otherwise associated with the dorsal aspect of the main bronchi. The lead can be attached to the electrode and can exit the thoracic cavity between the ribs. While other exit locations can be used, it can be convenient to use the existing access port. Once the lead exits the thoracic cavity, it can be tunneled subcutantiously to a convenient location for placing the implantable signal generator.

In the example of FIG. 7, the implantable signal generator is located in a low lumbar, pararenal location. In other examples, the implantable signal generator can be located in other locations in the body, such as in the thorax, or other subcutaneous locations. In other examples, the signal generator can be located outside of the body, with the lead exiting to connect externally.

Figure 8:
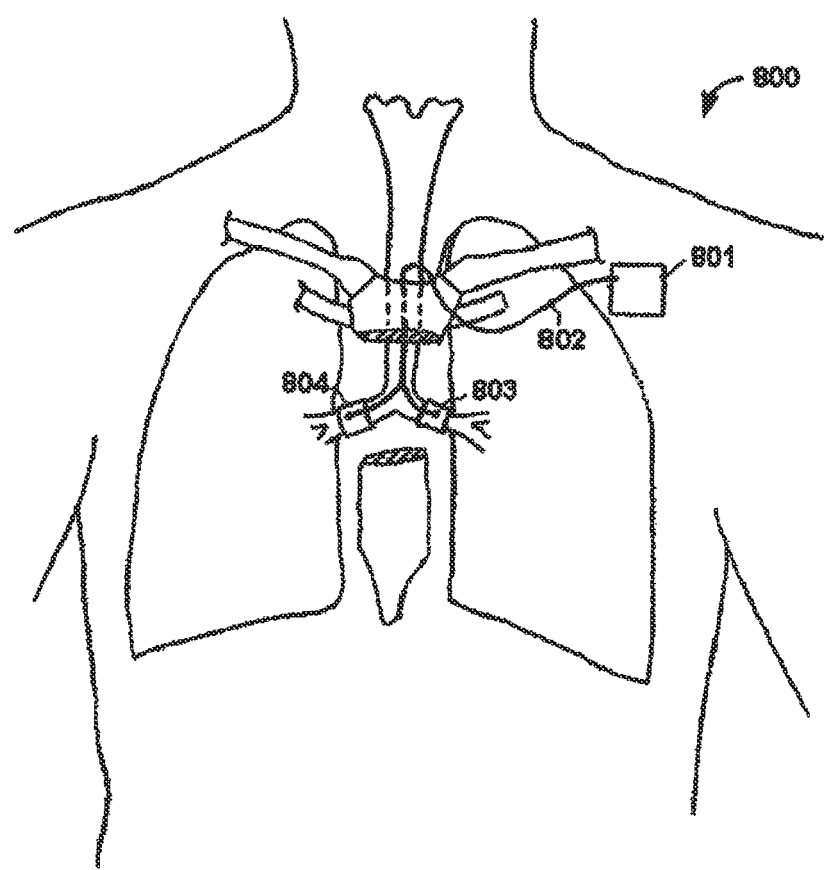

FIG. 8 illustrates generally an example of a system 800 including an implantable signal generator 801, a lead 802 coupled to the implantable signal generator 801, and first and second cuff electrodes 803, 804 coupled to the left and right bronchi.

Figure 9:
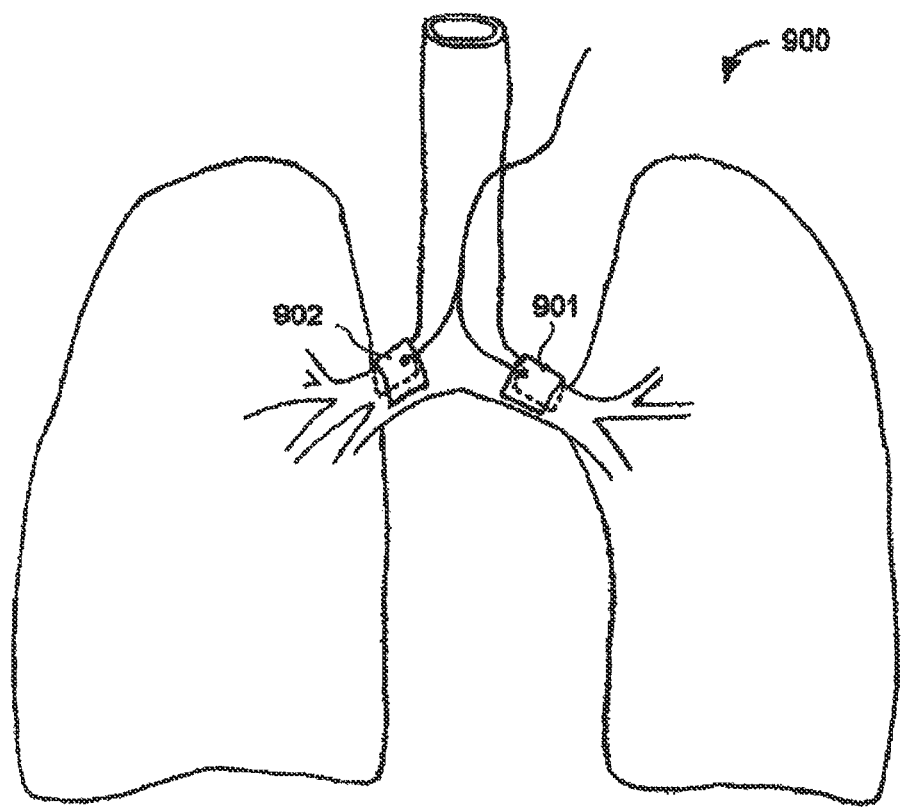

FIG. 9 illustrates generally an example of a system 900 including first and second partial cuff electrodes 901, 902 coupled to the left and right bronchi.

Figure 10:
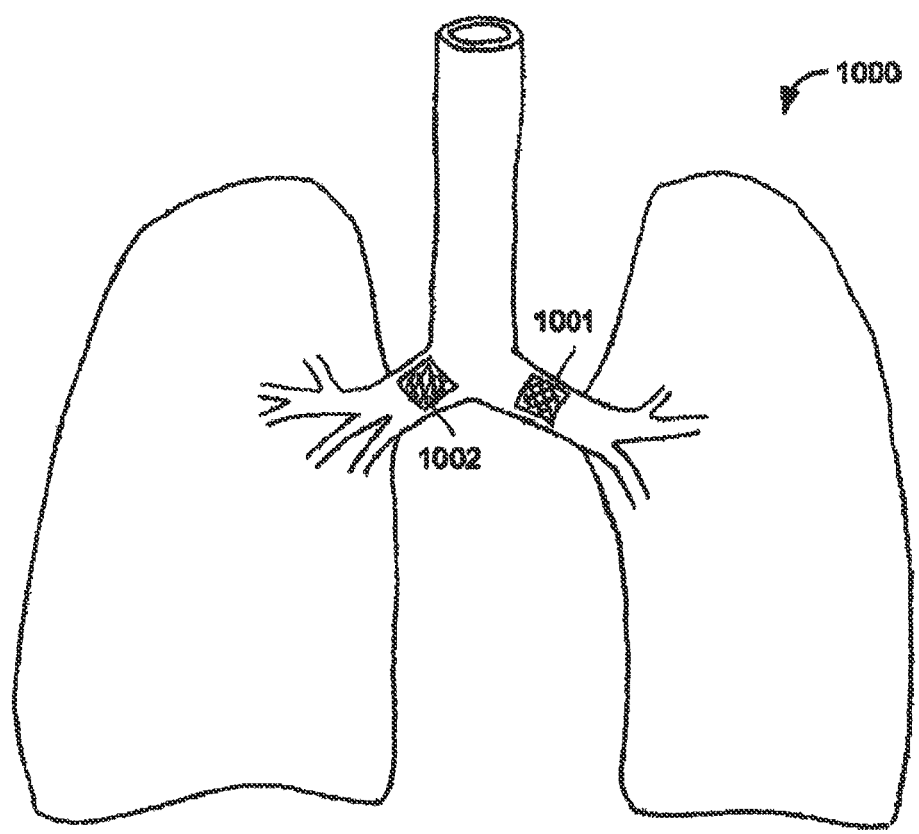

FIG. 10 illustrates generally an example of a system 1000 including first and second patch electrodes 1001, 1002 coupled to the left and right bronchi.

Figure 11A:
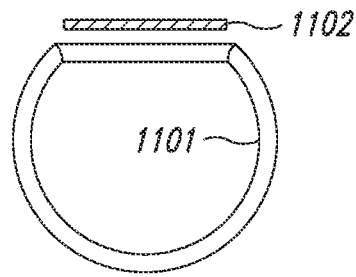
FIGS. 11A-11C illustrate generally example electrode configurations in, on, or surrounding at least a portion of a bronchus.
Figure 11B:
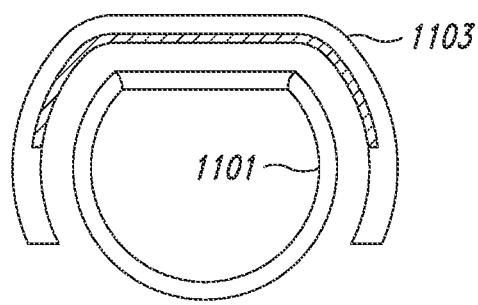
Figure 11C:
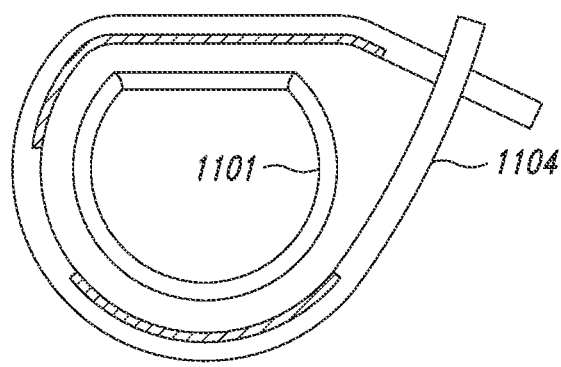

FIGS. 11A-11C illustrate generally example electrode configurations in, on, or surrounding at least a portion of a bronchus. FIG. 11A illustrates an example patch electrode configuration coupled to or near at least a portion of a dorsal side of a bronchus. FIG. 11B illustrates generally an example partial cuff electrode configuration coupled to or near the dorsal side of a bronchus. FIG. 11C illustrates generally an example full cuff electrode configuration coupled to, surrounding, or near at least a portion of a dorsal and ventral side of the bronchus. In other examples, other electrode configurations can be used. In an example, these, or other electrodes or electrode configurations, can be configured to be placed on the posterior (e.g., membranous aspect) of the bronchi.

Figure 12A:
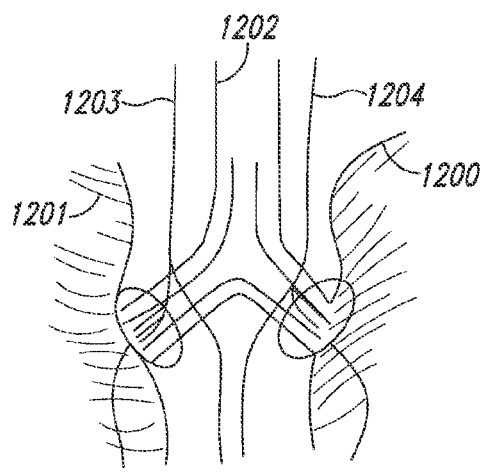
FIGS. 12A-12D illustrate generally an endo-bronchial electrode configuration and approach.

FIGS. 12A-12D illustrate generally an endo-bronchial electrode configuration and approach. FIG. 12A illustrates generally a dorsal view of a left lung 1200, a right lung 1201, a bronchi 1202, and pulmonary parasympathetic nerves 1203, 1204.

Figure 12B:
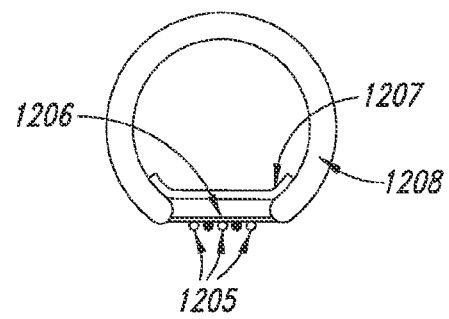

FIG. 12B illustrates generally an example of a wireless electrode 1206 and an antenna 1207 located in a trachea 1208 proximate pulmonary parasympathetic nerves 1205. In other examples, one or more wireless or other electrodes can be placed in the trachea 1208 or other location proximate the pulmonary parasympathetic sympathetic nerves 1205, or one or more other nerves.

Figure 12C:
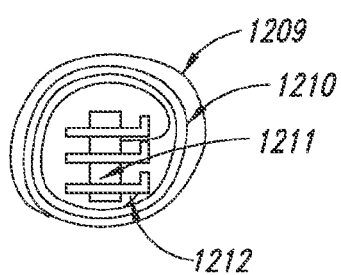

FIG. 12C illustrates generally an example of a silastic patch 1209, one or more electrodes 1212 (e.g., plunge or other electrodes), an embedded antenna 1210, and a control circuit 1211. In an example, the one or more electrodes 1212 can be sized or spaced be close to one or more dorsal pulmonary nerves, such as pulmonary parasympathetic nerves 1205.

Figure 12D:
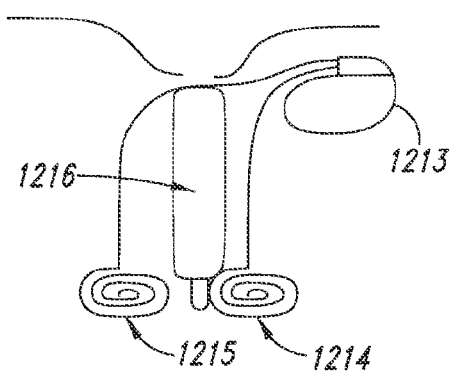

FIG. 12D illustrates generally an example of an implantable nerve stimulation pulse generator 1213 coupled (e.g., using one or more leads) to subcutaneously transmitting antennas 1214, 1215 on either side of a sternum 1216. In an example, the nerve stimulation pulse generator 1213 can be configured to deliver energy to one or more endo-bronchial electrode. In other examples, the endo-bronchial electrodes, such as the one or more electrodes 1212 can be configured to communicate with the nerve stimulation pulse generator 1213, or other implantable pulse generator, using the subcutaneously transmitting antennas 1214, 1215, or one or more other communication or telemetry devices.

Figure 13:
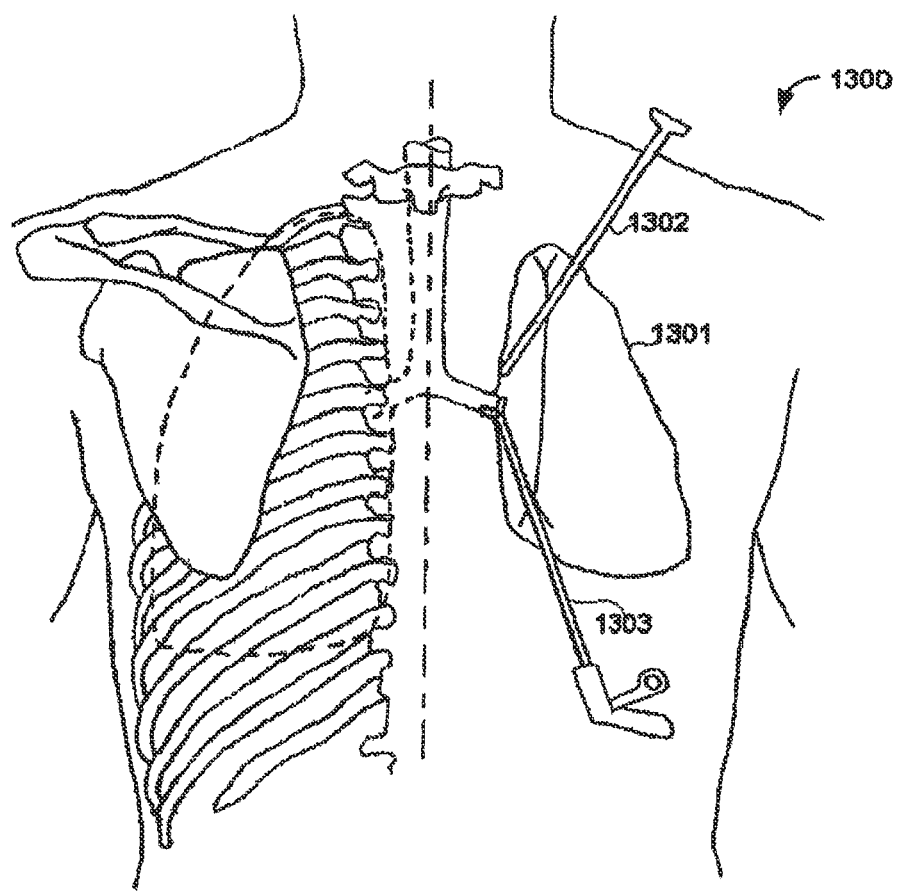
FIG. 13 illustrates generally a relationship between a bony structure and lungs, and an example of accessing the root of the main bronchi using two ports.

FIG. 13 illustrates generally a relationship between a bony structure and lungs, and an example of accessing the root of the main bronchi using two ports.

In an example, one or more ports can be placed between the ribs at any location between the shoulder blade and the spinal column, and from the second rib down to the tenth rib (typically at the fourth through eighth rib interspaces). In other examples, access can be gained lateral to the shoulder blade and along the anterior (i.e., ventral) aspect of the thorax.

In this example, a right lung 1301 is shown to be deflated and falling lateral and anterior within the thoracic cavity. In an example, the first port can be located approximately at the fourth rib interspace and the second port can be located approximately at the sixth rib interspace. Various instruments, such as a fiberscope 1302, a dissection tool 1303, etc., can be inserted through the first or the second port.

Other Examples

In an example, a system can include an implantable signal generator configured to generate a blocking signal to be delivered to at least a portion of a bronchus of a subject. In an example, the blocking signal can be configured to inhibit nerve traffic both to and from a lung of the subject, to relieve bronchial smooth muscle contraction, and to inhibit cough and mucus production.

In certain examples, the system can include a mucus sensor, configured to detect an indication of mucus buildup in at least a portion of the bronchus. Further, the system can include a processor, communicatively coupled to the implantable signal generator and the mucus sensor, the processor configured to control delivery of the blocking signal, and to stop delivery of the blocking signal, using the indication of mucus buildup, to allow mucus clearance.

In this example, the blocking signal can be provided for sustained periods of time, or according to one or more therapy algorithms (e.g., having a duty cycle, a scheduled "on" and "off" time, etc.). If the indication of mucus buildup is received, the therapy algorithm can be interrupted to provide for a period of no blocking signal, configured to allow cough and clear built up mucus.

Further, in certain examples, the blocking signal can be provided to inhibit mucus production.

Some Notes

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, the code may be tangibly stored on one or more volatile or non-volatile computer-readable media during execution or at other times. These computer-readable media may include, but are not limited to, hard disks, removable magnetic disks, removable optical disks (e.g., compact disks and digital video disks), magnetic cassettes, memory cards or sticks, random access memories (RAM's), read only memories (ROM's), and the like. Further, in certain examples, a processor configured to perform a function or operation can include one or more processors, each configured to perform at least a portion of the function or operation.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A method of reducing bronchial constriction in a subject, comprising:

delivering energy so as to damage pulmonary nerves located along an airway in the subject sufficiently to reduce bronchial constriction in a lung of the patient; and preventing re-innervation of the pulmonary nerves.

2. The method of claim 1, wherein the preventing re-innervation of the pulmonary nerves includes transecting the pulmonary nerves of the subject at a plurality of locations by creating a series of lesions.

3. The method of claim 2, wherein the plurality of locations are positioned around at least a portion of a circumference the airway of the subject.

4. The method of claim 2, wherein transecting the pulmonary nerves includes transecting the pulmonary nerves using electrocautery.

5. The method of claim 2, wherein the series of lesions includes two or more lesions separated by 2 mm to 15 mm gaps.

6. The method of claim 2, wherein the series of lesions are linear.

7. The method of claim 1, wherein preventing re-innervation of the pulmonary nerves includes attaching an implant on the bronchus to prevent the damaged nerves from reinnervating.

8. The method of claim 7, wherein the implant includes a bioactive component that suppresses neuron growth or regeneration.

9. The method of claim 1, wherein preventing re-innervation of the pulmonary nerves includes implanting an active stimulation system that substantially inhibits nerve signals at the airway to block both outgoing and incoming signals from the lungs to maintain the reduced bronchial constriction in the lung of the patient.

* * * * *